United States Patent
Letton et al.

(10) Patent No.: US 10,368,502 B2
(45) Date of Patent: Aug. 6, 2019

(54) BIOCERAMIC AND CARBON-BASED HYDROPONIC SYSTEMS, METHODS AND DEVICES

(71) Applicant: MULTIPLE ENERGY TECHNOLOGIES LLC, Washington, PA (US)

(72) Inventors: Alan Letton, Greensboro, NC (US); Ross A. Marino, McMurray, PA (US); Francisco Jose Cidral-Filho, Washington, PA (US); Shannon Vissman, Upper St. Clair, PA (US)

(73) Assignee: MULTIPLE ENERGY TECHNOLOGIES LLC, Washington, PA (US)

( * ) Notice: Subject to any disclaimer, the term of this patent is extended or adjusted under 35 U.S.C. 154(b) by 0 days.

(21) Appl. No.: 15/899,882

(22) Filed: Feb. 20, 2018

(65) Prior Publication Data
US 2019/0090438 A1    Mar. 28, 2019

Related U.S. Application Data

(60) Provisional application No. 62/562,971, filed on Sep. 25, 2017.

(51) Int. Cl.
*A01G 24/15* (2018.01)
*A61K 36/185* (2006.01)
*A01G 22/00* (2018.01)

(52) U.S. Cl.
CPC ............ *A01G 24/15* (2018.02); *A01G 22/00* (2018.02); *A61K 36/185* (2013.01)

(58) Field of Classification Search
CPC ......... A01G 24/15; A01G 24/12; A01G 24/10
See application file for complete search history.

(56) References Cited

U.S. PATENT DOCUMENTS

| | | |
|---|---|---|
| 4,968,531 A | 11/1990 | Maeda |
| 2002/0014716 A1 | 2/2002 | Seok |
| 2005/0171584 A1 | 8/2005 | Slingo |
| 2007/0116775 A1 | 5/2007 | Lee |
| 2009/0171266 A1 | 7/2009 | Harris |
| 2010/0281936 A1* | 11/2010 | Lee ............... A01G 24/00 71/47 |
| 2011/0059037 A1 | 3/2011 | Canova et al. |
| 2011/0112461 A1 | 5/2011 | Hirata |
| 2011/0208099 A1 | 8/2011 | Naghavi et al. |
| 2012/0135485 A1 | 5/2012 | Koros et al. |
| 2013/0172185 A1* | 7/2013 | Wei ............... A01N 37/46 504/127 |
| 2014/0079920 A1 | 3/2014 | Blakely |
| 2014/0087040 A1 | 3/2014 | Vissman et al. |
| 2014/0209594 A1 | 7/2014 | Besner |
| 2018/0055933 A1 | 3/2018 | Vissman et al. |

FOREIGN PATENT DOCUMENTS

| | | |
|---|---|---|
| CN | 2568221 Y | 8/2003 |
| CN | 102553623 A | 7/2012 |
| JP | 2001192257 A | 7/2001 |
| JP | 2004359811 A | 12/2004 |
| JP | 2008308353 A | 12/2008 |
| JP | 2008308354 A | 12/2008 |
| JP | 2010212156 A | 9/2010 |
| JP | 2011506668 A | 3/2011 |
| KR | 20050046213 A | 5/2005 |
| KR | 20090098932 A | 9/2009 |
| KR | 101067409 B1 | 9/2011 |
| WO | WO-2015171467 A1 | 11/2015 |

OTHER PUBLICATIONS

Chinese Patent Application No. 2015800367193 Office Action dated May 2, 2018.
European Patent Application No. 13842936.0 Office Action dated Apr. 3, 2018.
International Application No. PCT/US2013/060636 International Preliminary Report on Patentability dated Mar. 31, 2015. 0.
International Application No. PCT/US2013/060636 International Search Report and Written Opinion dated Jan. 10, 2014.
Japanese Patent Application No. 2015-534562 Office Action dated May 7, 2018.
Lai et al., Effects of far-infrared irradiation on myofascial neck pain: A randomized, double-bind, placebo-controlled pilot study The Journal of Alternative and Complementary Medicine, 0(0):1-7 (2013).
Leung et al., Physiological effects of bioceramic material: Harvard step, resting metabolic rate and treadmill running assessments. Chinese Journal of Physiology, 56(x):1-7 (2013).
PCT/US2015/028910 International Search Report and Written Opinion dated Sep. 1, 2015.
Tuduvz, LLC, Far Infrared therapy: Healing with far infrared therapy Website (online), Apr. 13, 2014 (retrieved on Aug. 11, 2015), www.endtimeessentials.com/far-infrared-therapy, 3 pages.

* cited by examiner

*Primary Examiner* — Kristen C Hayes
(74) *Attorney, Agent, or Firm* — Wilson Sonsini Goodrich & Rosati

(57) ABSTRACT

Described herein are methods, compositions, products, and processes that utilize bioceramics in traditional agricultural and hydroponic systems. The bioceramics are utilized in powder form, as films, as aerosols, as water based treatment systems, or in solid forms. The methods and bioceramic compositions described here are also used for growing a *Cannabis* plant. One or more cannabinoids within the plant can be used in therapeutic compositions for the treatment of glaucoma, AIDS wasting syndrome, neuropathic pain, cancer, multiple sclerosis, chemotherapy-induced nausea, and certain seizure disorders.

15 Claims, 10 Drawing Sheets

Panel A

Panel B

BIOCERAMIC AND CARBON-BASED HYDROPONIC SYSTEMS, METHODS AND DEVICES

CROSS REFERENCE

This application claims the benefit of U.S. Provisional Application No. 62/562,971, filed Sep. 25, 2017 which application is incorporated herein by reference.

BACKGROUND

Agriculture is the cultivation and breeding of animals, plants and fungi for food, fiber, biofuel, medicinal plants and others. The dominant agricultural methodology in modern times, often referred to as industrial agriculture, is typically based on large-scale monoculture farming and usually involves plant breeding, agrochemicals such as pesticides and fertilizers, and technological developments that have in many cases sharply increased yields from cultivation, while causing widespread ecological damage and negative human health effects. Over one third of the world's workers are employed in agriculture, and not surprisingly agricultural food production and water management are increasingly becoming global issues.

SUMMARY

Described herein are methods, compositions, products, and processes that utilize bioceramics in traditional agricultural, hydroponic, and aquaponic systems. The disclosure provides bioceramics and devices comprising bioceramics that can be used to enhance organoleptic properties of a plant, to increase an amount of an active ingredient of a plant, or generally to improve the growth of a plant. These devices can be, for example, cloths or textiles impregnated with a bioceramic, solid form bioceramic devices that are sintered and molded forms of the bioceramic, or as devices that are manufactures as layered or non-layered filters for water treatment. The bioceramics described herein are also utilized in powder form, as films, as aerosols, as water based treatment systems, or in other suitable forms. The methods and bioceramic compositions are used for growing a plant, such as a plant that can produce one or more active ingredients for use as drugs and medicines. The plant can be a *Cannabis* plant, an ornamental plant, or another plant used in agriculture.

Generally, the disclosure provided herein provides a bioceramic that can be used to enhance organoleptic properties of a plant, to increase an amount of an active ingredient of a plant, or generally to improve the growth of a plant. The plant can be, for example, a plant that produces a food crop, such as rice, wheat, maize, sorghum, ragi, legumes, fruits, vegetables, soybeans, or nuts, soybeans. A plant can be an ornamental plant, such as plants that are used in gardens and landscape design projects, houseplants, ornamental flowering flowers and others. In some cases, a plant can be a plant that produces one or more active compound that can have a medicinal effect.

In some cases, described herein is a method of growing a plant from the Cannabaceae family on a substrate, the method comprising: cultivating the plant from the Cannabaceae family on the substrate, wherein the substrate comprises: a) at most 1 part of a kaolinite to 100 parts of the substrate; and b) at most 1 part of a tourmaline to 100 parts of the substrate. In some cases, the substrate comprises at most 1 part per volume of a kaolinite to 100 parts per volume of the substrate, at most 1 part per weight of a kaolinite to 100 parts per weight of the substrate, at most 1 part per weight of a kaolinite to 100 parts per volume of the substrate, or at most 1 part per volume of a kaolinite to 100 parts per weight of a substrate. In some cases, the substrate comprises at most 1 part per volume of a tourmaline to 100 parts per volume of the substrate, the substrate comprises at most 1 part per weight of a tourmaline to 100 parts per weight of the substrate, at most 1 part per weight of a tourmaline to 100 parts per volume of the substrate, or at most 1 part per volume of a tourmaline to 100 parts per weight of a substrate. In some cases the plant from the Cannabaceae family is a plant from the *Cannabis* genus. The *Cannabis* plant can be a *Cannabis sativa* plant, a *Cannabis indica* plant, or a hybrid plant of two or more *Cannabis* species. In some instances the presence of the kaolinite and the tourmaline on the substrate modulates a phytocannabinoid profile of the *Cannabis* plant, such as an amount of a tetrahydrocannabinol (THC) in the *Cannabis* plant, an amount of a Cannabidiol (CBD) in the *Cannabis* plant, or an amount of a delta-8-tetrahydrocannabinol, a cannabinol (CBN), a cannabicyclol (CBL), a cannabichromene (CBC), or a cannabigerol (CBG). In some instances the substrate is a soil. In other instances the substrate is a water solvent comprising mineral nutrients. In some instances the substrate comprises less than 10% dry weight of nitrogen (N), phosphorus (P), potassium (K), calcium (Ca), sulfur (S), magnesium (Mg), and sodium (Na); or less than 0.01% dry weight of one or more trace minerals selected from the group consisting of: boron (B), chlorine (CO, manganese (Mn), iron (Fe), zinc (Zn), copper (Cu), molybdenum (Mo), nickel (Ni), and cobalt (Co). In some instances, the substrate further comprises at least one oxide selected from the group consisting of silicon dioxide ($SiO_2$), aluminum oxide ($Al_2O_3$), titanium dioxide ($TiO_2$), and magnesium oxide (MgO). In some instances, the methods disclosed herein further comprise adding a second quantity of a kaolinite and a second quantity of tourmaline to the substrate after a first period of time. The first period of time can be from 7 days to 80 days, from 20 days to 60 days, or from 20 days to 40 days. In some instances, the methods disclosed herein further comprise adding a third quantity of a kaolinite and a third quantity of tourmaline to the substrate to the substrate after a second period of time. The second period of time can be from 7 days to 160 days, from 20 days to 140 days, from 20 days to 120 days, from 20 days to 100 days, from 20 days to 80 days, from 20 days to 60 days, from 20 days to 40 days after the first period of time. The cultivating can increase a total number of flowers, a total number of leaves, or a total weight of the Cannabaceae plant as compared to a control. The cultivating can also increase a partial weight of the Cannabaceae plant, not including the weight of the roots, as compared to a control.

A medicinal formulation comprising at least a portion of a Cannabaceae plant grown according to the methods described herein. The at least a portion of the Cannabaceae plant can comprise a leave, a flower, a steam, a bud, or a seed. The plant from the Cannabaceae family can be a plant from the *Cannabis* genus, such as a *Cannabis sativa* plant, a *Cannabis indica* plant, or a hybrid plant of two or more *Cannabis* species. In some instances, one or more cannabinoids within the plant can be used in therapeutic compositions for the treatment of glaucoma, AIDS wasting syndrome, neuropathic pain, cancer, multiple sclerosis, chemotherapy-induced nausea, and certain seizure disorders.

BRIEF DESCRIPTION OF THE DRAWINGS

The novel and inventive features of the invention are set forth with particularity in the appended claims. A better understanding of the features and advantages of the present invention will be obtained by reference to the following detailed description that sets forth illustrative embodiments, in which the principles of the invention are utilized, and the accompanying drawings which in this patent application are provided in the Examples section below.

FIG. 2, Panel A illustrates a soil substrate comprising about 1 part volume of a bioceramic to about 9 parts volume of the substrate. FIG. 2, Panel B illustrates a water substrate comprising about 1 part volume of a bioceramic to about 9 parts volume of the substrate.

DETAILED DESCRIPTION

Figure 1:
FIG. 1 illustrates a root system of a Cannabaceae plant, *Cannabis indica* grown in a soil substrate as described herein.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

Overview

Bioceramics and Products Comprising Bioceramics for Use in Plant Growth

Provided herein are far-infrared energy emitting bioceramics for use in agricultural, hydroponic, and aquaponic systems. The instant bioceramics comprise kaolinite and tourmaline minerals and oxides that are highly refractory and absorb high amounts of far-infrared energy. Such far infrared energy has the ability to penetrate, refract, radiate, and reflect energy to living cells. Those far infrared rays can promote the growth and health of living cells, especially in plants.

A disclosed bioceramic can be used, for example, in an agricultural setting to improve the growth of a plant. Major agricultural products can be broadly grouped into foods, fibers, fuels, and raw materials. Non-limiting examples of specific foods include cereals (grains), vegetables, fruits, oils, meats and spices. Fibers include cotton, wool, hemp, silk and flax. Raw materials include, for example, lumber and bamboo. Other useful materials are also produced by plants, such as resins, dyes, perfumes, biofuels and ornamental products such as cut flowers and nursery plants, and notably medicinal drugs.

In some instances, the bioceramic can be formed into any number of devices which then release the bioceramic over time through specific processes. Such devices can be fabricated by sintering, for example, a powdered bioceramic into a shape, co-mingling a bioceramic into a shape with one or more materials, adding the bioceramic into a mold that can be pressed into the ground, or another suitable method that can expose the roots of a plant to the bioceramic and its far-infrared energy, thereby enhancing plant growth. In some aspects, the device can be fabricated by injection molding. Injection molding can be performed with a host of materials such as metals, glasses, elastomers, confections, and most commonly thermoplastic and thermosetting polymers. Material for the part is often inserted into a heated barrel, mixed, and forced into a mold cavity, where it cools and hardens to the configuration of the cavity. After a product is designed, usually by an industrial designer or an engineer, molds are made by a mold-maker (or toolmaker) from metal, which can be a metal—such as steel or aluminum—and precision-machined to form the features of the desired part. In some aspects, the disclosure provides ground penetrating devices (stakes) made from the disclosed bioceramics. In other aspects, the device comprises other molded devices comprising sintered bioceramics of the disclosure. Non-limiting examples of other molded devices can include, pots, trays, buckets, saucers, basket liners, net pots, tray inserts, mats, and other containers. The different devices may release a bioceramic through different mechanisms. Non-limiting examples of the mechanisms through which the bioceramic may be released are gravity, humidity, leaching, filtering, straining, percolating, heating, and/or pressure.

In other aspects, the disclosure provides an aerosol based system where the bioceramic particles are suspended and can, for instance, be distributed to a plant as fine particles. In yet other aspects, the disclosure provides a formulation of a bioceramic as a film that can be delivered to a surface. In such instances, the bioceramic can be formulated with one or more film forming agents that provide a pliable, cohesive, and continuous film.

In some instances, the disclosure provides a fabric or a textile that is fabricated by a suitable method where color pigments are either replaced or co-mingled with the disclosed bioceramics. These products can "camouflage" the soil with a "mulch" look where the printed bioceramic is contained within. Examples of these methods include silk-screen printing process, a dot application process, a binder solution application process, a visible repeating pattern process or any other suitable method can be employed. Non-limiting examples of printing processes can be found in PCT/US15/28910, filed on May 1, 2015, which is incorporated herein by reference in its entirety. The disclosure also provides products for use in agriculture that are fabricated via a screen print method onto a textile that controls the deposition of bioceramic powder on the textile. The printing can occur in layers of the textile (for example, lawyers of a non-woven textile). Such layers can be stacked to create a filter for water treatment or can be corrugated to create a pass-thru filter for water treatment.

The disclosed bioceramics can be formulated for application to a plant in the form of a powder, an aerosol, a mist, a sintered form, or in another suitable form. Tourmaline and kaolinite have distinct granulometric, mineralogical, chemical, and physical properties depending on, for example, whether the minerals are extracted from a particular geographic region or whether the minerals are chemically synthesized. For instance, in many parts of the world a kaolinite has a pink-orange-red coloration that is associated with an amount of an impurity(ies). Often, the impurity(ies) comprises iron oxide. In some embodiments, a kaolinite of the disclosure is of a high purity level, and it is characterized by a fine white color. Furthermore, tourmaline is a hard material with a Mohs hardness scale of between 7-7.5 Mohs whereas kaolinite is a soft material with a Mohs hardness scale of between 2-2.5 Mohs.

In some instances, the disclosed bioceramic formulations are pre-mixed and prepared as a powder formulation. In other instances, the individual components of a bioceramic can be separately added to a substrate. In some instances, the bioceramic formulations described herein generally comprise from about 20 wt % to about 80 wt % kaolinite ($Al_2Si_2O_5(OH)_4$), from about 1 wt % to about 30 wt % tourmaline, and at least one additional oxide from about 1 to 19% wt %, provided that the amounts are by total weight of the bioceramic composition. The at least one additional oxide can be selected from the group consisting of aluminum oxide ($Al_2O_3$), silicon dioxide ($SiO_2$), titanium dioxide ($TiO_2$), magnesium oxide (MgO), and zirconium dioxide ($ZrO_2$).

In some instances, the bioceramic composition comprises from about 40 wt % to about 60 wt % kaolinite ($Al_2Si_2O_5(OH)_4$) to about 5 wt % to about 15 wt % tourmaline to about 15 wt % to about 25 wt % aluminum oxide ($Al_2O_3$) to about 10 wt % to about 20 wt % silicon dioxide ($SiO_2$); and from about 1 wt % to about 20 wt % titanium dioxide ($TiO_2$); provided that the total amounts are by total weight of the composition.

In other instances, the bioceramic composition comprises from about 40 wt % to about 60 wt % kaolinite ($Al_2Si_2O_5(OH)_4$) to about 5 wt % to about 15 wt % tourmaline to about 15 wt % to about 25 wt % aluminum oxide ($Al_2O_3$) to about 10 wt % to about 20 wt % silicon dioxide ($SiO_2$); and from about 1 wt % to about 20 wt % magnesium oxide (MgO); provided that the total amounts are by total weight of the composition.

In some instances, the bioceramic composition comprises from about 40 wt % to about 60 wt % kaolinite ($Al_2Si_2O_5(OH)_4$) to about 5 wt % to about 15 wt % tourmaline to about 15 wt % to about 25 wt % aluminum oxide ($Al_2O_3$) to about 10 wt % to about 20 wt % silicon dioxide ($SiO_2$); and from about 1 wt % to about 20 wt % zirconium dioxide ($ZrO_2$); provided that the total amounts are by total weight of the composition.

In other instances, the individual components of a bioceramic can be separately added to a substrate. FIG. 2 illustrates exemplary powdered bioceramics mixed with soil and water substrates.

One or more components of the disclosed bioceramics may be ground to a coarse, or to a fine form in a powder. In some embodiments, a granularity of a kaolinite or a tourmaline in one or more of the products described herein is associated with an amount of infrared energy that is radiated from a bioceramic composition. For instance, a bioceramic composition comprising coarser-size mineral can reflect a different amount of infrared energy as compared to a bioceramic composition comprising finer-size minerals. In some embodiments, the granularity of a bioceramic composition ranges from about 100 nanometers to about 0.1 micrometers, from about 100 nanometers to about 1 micrometer, from about 100 nanometers to about 10 micrometers, from about 100 nanometers to about 25 micrometers, from about 100 nanometers to about 50 micrometers, from about 100 nanometers to about 75 micrometers, from about 100 nanometers to about 100 micrometers, from about 100 nanometers to about 125 micrometers, from about 100 nanometers to about 150 micrometers, from about 100 nanometers to about 175 micrometers, from about 100 nanometers to about 200 micrometers, from about 100 nanometers to about 225 micrometers, or from about 100 nanometers to about 250 micrometers.

In some embodiments, the granularity of a bioceramic composition ranges from about 0.5 micrometers to about 1 micrometer, from about 0.5 micrometers to about 10 micrometers, from about 0.5 micrometers to about 25 micrometers, from about 0.5 micrometers to about 50 micrometers, from about 0.5 micrometers to about 75 micrometers, from about 0.5 micrometers to about 100 micrometers, from about 0.5 micrometers to about 125 micrometers, from about 0.5 micrometers to about 150 micrometers, from about 0.5 micrometers to about 175 micrometers, from about 0.5 micrometers to about 200 micrometers, from about 0.5 micrometers to about 225 micrometers, or from about 0.5 micrometers to about 250 micrometers.

The disclosure also provides sintered formulations of a bioceramic. Sintering is the process of compacting and forming a solid mass of material by heat or pressure without melting it to the point of liquefaction. Sintering can be an effective way of reducing the porosity of a composition, or enhancing properties such as thermal conductivity, strength, electrical conductivity, and translucency. In some cases, a bioceramic composition disclosed herein is sintered into a shape. The bioceramic composition can be sintered into a variety of regular or irregular cross-sectional shapes such as, for example, a stake shape, a circular, a half-circular, a diamond, a hexagonal, a multi-lobal, an octagonal, an oval, a pentagonal, a rectangular, a square, a star-shaped, a trapezoidal, a triangular, a wedge-shaped, or another suitable shape that can be added to a substrate to support the growth of a bioceramic.

The disclosure also provides aerosol formulations of a bioceramic. In some cases the bioceramic is prepared as an aerosol based system where the bioceramic particles are suspended in a film former and delivered to a surface. In some cases, the bioceramic compositions have ultra-fine particles.

In some instances, the average diameter, or cross-sectional area, of a particle in a bioceramic composition described herein, is from about 0.1 μm to about 1 μm, of about 0.1 μm to about 10 μm, of about 0.1 μm to about 20 μm, of about 0.1 μm to about 30 μm, of about 0.1 μm to about 40 μm, of about 0.1 μm to about 50 μm, of about 0.1 μm to about 60 μm, of about 0.1 μm to about 70 μm, of about 0.1 μm to about 80 μm, of about 0.1 μm to about 90 μm, of about 0.1 μm to about 100 μm, or other desired size. In some cases, the bioceramics have a cross-sectional diameter of about 10 μm to about 100 μm, of about 10 μm to about 200 μm, of about 10 μm to about 300 μm, of about 10 μm to about 400 μm, of about 10 μm to about 500 μm, or other desired size.

In some cases the average density of a bioceramic particle described herein is from about 2 grams/$cm^3$ to 3 about grams/$cm^3$, from about 2.1 grams/$cm^3$ to 2.9 about grams/$cm^3$, from about 2.2 grams/$cm^3$ to 2.8 about grams/$cm^3$, from about 2.3 grams/$cm^3$ to 2.7 about grams/$cm^3$, from about 2.4 grams/$cm^3$ to 2.6 about grams/$cm^3$. In some cases the average density of a bioceramic particle described herein is about 2.5 grams/$cm^3$. In some cases the average density of a bioceramic particle described herein is from about 2 grams/$cm^3$ to 3 about grams/$cm^3$, from about 2.1 grams/$cm^3$ to 2.9 about grams/$cm^3$, from about 2.2 grams/$cm^3$ to 2.8 about grams/$cm^3$, from about 2.3 grams/$cm^3$ to 2.7 about grams/$cm^3$, from about 2.4 grams/$cm^3$ to 2.6 about grams/$cm^3$. In some cases the mean density of a bioceramic particle described herein is about 2.5 grams/$cm^3$.

In some cases, a bioceramic product can be incorporated into a filter, a mesh, a sifter, or another suitable fabric or textile that allows the passage of a desired particle size through the filter, the mesh, or the sifter while blocking the passage of particles of an undesired size. A fabric can be a porous mesh. A fabric can comprise a plurality of sheets that can be layered to create a filter with a desired thickness, porosity, or another suitable property. In some cases, a fabric, or various sheets of fabric, is/are configured to for a filter, or to be placed within a receptacle that supports the growth of a plant, i.e., a pot or a hydroponics support system.

In some embodiments, a purity of the tourmaline or kaolinite is associated with an amount of infrared energy that is radiated from a bioceramic composition. In some cases the kaolinite or tourmaline of a bioceramic composition of the disclosure is greater than 99% pure, greater than 98% pure, greater than 97% pure, greater than 96% pure, greater than 95% pure, greater than 94% pure, greater than 93% pure, greater than 92% pure, greater than 91% pure, greater than 90% pure, greater than 89% pure, greater than 88% pure, greater than 87% pure, greater than 86% pure, greater than 85% pure, greater than 80% pure, greater than 75% pure, greater than 70% pure, greater than 65% pure, greater than 60% pure, or greater than 55% pure.

Cannabaceae Family of Plants

Long before pure chemicals were manufactured in labs, people used plants for medicine. In the United States, the federal Controlled Substances Act (CSA) controls substances that are psychoactive or otherwise have abuse potential. The CSA controls all stages of the manufacturing and supply chain. The extent or stringency of these controls is largely determined by a substance's classification in one of five schedules for controlled substances. Schedule I substances like *cannabis* and cannabinoids cannot be prescribed and can only be lawfully dispensed and possessed as part of a federally approved research program.

Investigators interested in conducting research on *cannabis* plant material typically must obtain that *cannabis* through the National Institute on Drug Abuse (NIDA), which cultivates different varieties of research-grade *cannabis* with various tetrahydrocannabinol (THC) to cannabidiol CBD ratios. Nevertheless, the approval of Dronabinol (a synthetic cannabinoid designated chemically as (6aR-trans)-6a,7,8,10a-tetrahydro-6,6,9-trimethyl-3-pentyl-6H-dibenzo[b,d]pyran-1-ol) for the treatment of nausea and vomiting caused by cancer chemotherapy, as well as loss of appetite and weight loss in patients with HIV infection, indicates that there may be viable, safer, alternatives to the use of opioids in the treatment of those conditions.

Without being limited by theory the instant inventors have discovered that a combination of tourmaline, kaolinite, and optionally at least one additional oxide can improve the growth and properties of a plant of the Cannabaceae family. The task of categorizing and cataloguing the billions of existing plant species is vastly complex. Phylogenetics approaches have been employed to categorize plant species based on genetic similarity. Nevertheless, according to the Integrated Taxonomic Information System (ITIS), the Cannabaceae family is a small family of flowering plants. As now circumscribed, the family includes about 170 species grouped in about 11 genera, including *Cannabis* (hemp, marijuana), *Humulus* (hops) and *Celtis* (hackberries). *Celtis* is by far the largest genus, containing about 100 species. The Cannabaceae family, along with three other families, makes up the (informal) suborder Urticalean rosids, of the order Rosales. Along with the Urticalean rosids, another five families belong to the Rosales order; these include Rosaceae (rose) and Rhamnaceae (buckthorn). Among the plants in the Cannabaceae family, the *Cannabis* genus is apparently unique within the Cannabaceae family for containing cannabinoids.

As described herein the number of species within the *Cannabis* genus includes *Cannabis sativa, Cannabis indica, Cannabis ruderalis*, and hybrids of the same, all of which contain cannabinoids. A cannabinoid is one of a class of diverse chemical compounds that acts on cannabinoid receptors in cells that alter neurotransmitter release in the brain. Ligands for these receptor proteins include the endocannabinoids (produced naturally in the body by animals), the phytocannabinoids (found in *Cannabis* and others), and synthetic cannabinoids (manufactured artificially). The most notable cannabinoid is the phytocannabinoid tetrahydrocannabinol (THC), the primary psychoactive compound in *Cannabis*. Cannabidiol (CBD) is another major constituent of the plant. There are at least another 113 different cannabinoids isolated from *Cannabis*, exhibiting varied effects.

Further described herein are methods and compositions for growing a *Cannabis* plant that modulate an amount of one or more cannabinoids within the plant. The compositions disclosed herein can be used for the treatment of glaucoma, AIDS wasting syndrome, neuropathic pain, cancer, multiple sclerosis, chemotherapy-induced nausea, and certain seizure disorders. In some instances the cannabinoid is tetrahydrocannabinol, as illustrated below:

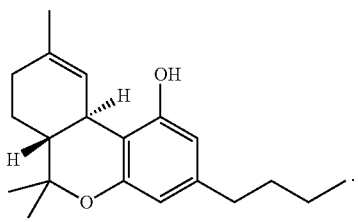 [SMILES: CCCCc1cc(O)c2c(c1)OC(C)(C)[C@@H]1CCC(C)=C[C@@H]21]

Tetrahydrocannabinol is the most abundant psychoactive cannabinoid in *Cannabis* plants. As used herein, tetrahydrocannabinol generally refers to both $\Delta^9$-Tetrahydrocannabinol ($\Delta^9$-THC) and $\Delta^8$-Tetrahydrocannabinol ($\Delta^8$-THC). Tetrahydrocannabinol can be used to treat glaucoma, pain, nausea, vomiting, asthma, post-traumatic stress disorder (PTSD), and others. It can also be used as an appetite stimulant. In some instances the cannabinoid is $\Delta^9$-Tetrahydrocannabinol ($\Delta^9$-THC) or $\Delta^8$-Tetrahydrocannabinol ($\Delta^8$-THC), as illustrated below:

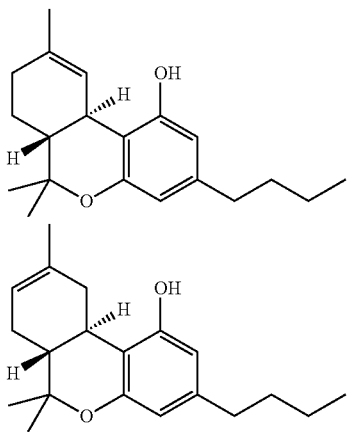

The cannabinoid can be cannabidiol (CBD). Cannabidiol can be used to treat epilepsy, schizophrenia, and a number of other conditions. In some instances the cannabinoid is cannabidiol, as illustrated below:

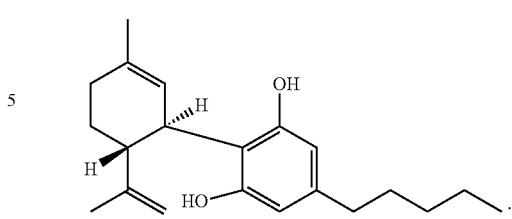

The cannabinoid can be cannabinol (CBN). Oxidation of THC can lead to the conversion of THC into CBN. In some instances the cannabinoid is cannabinol, as illustrated below:

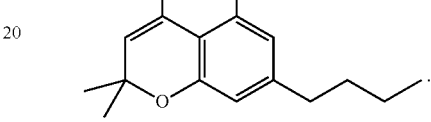

The cannabinoid can be a precursor for THC or CBN, such as, for example, cannabigerol (CBG), illustrated below:

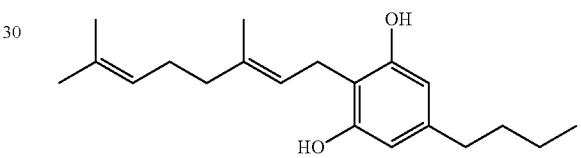

Cannabigerol is a non-psychoactive cannabinoid, and it is the building block for THC and CBD. Cannabigerol can be used in a medicinal formulation to reduce intraocular pressure, which can be used to treat glaucoma patients.

TABLE 1 illustrates compounds isolated from *Cannabis* plants and non-limiting examples of their pharmacological and medicinal uses.

TABLE 1

| Compound | Structure | Main pharmacological characteristics |
|---|---|---|
| Cannabigerol class | | |
| Cannabigerolic acid (CBGA) | $R_1$ = COOH, $R_2$ = $C_5H_{11}$, $R_3$ = H | Antibiotic |
| Cannabigerolic acid monomethylether (CBGAM) | $R_1$ = COOH, $R_2$ = $C_5H_{11}$, $R_3$ = $CH_3$ | |
| Cannabigerol (CBG) | $R_1$ = H, $R_2$ = $C_5H_{11}$, $R_3$ = H | Antibiotic, Antifungal, Anti-inflammatory, analgesic |

TABLE 1-continued

| Compound | Structure | Main pharmacological characteristics |
|---|---|---|
| Cannabigerol monomethylether (CBGM) | $R_1 = H, R_2 = C_5H_{11}, R_3 = CH_3$ | |
| Cannabigerovarinic acid (CBGVA) | $R_1 = COOH, R_2 = C_3H_7, R_3 = H$ | |
| Cannabigerovarin (CBGV) | $R_1 = H, R_2 = C_3H_7, R_3 = H$ | |

Cannabichromene class

| Cannabichromenic acid (CBCA) | $R_1 = COOH, R_2 = C_5H_{11}$ | |
|---|---|---|
| Cannabichromene (CBC) | $R_1 = H, R_2 = C_5H_{11}$ | Antibiotic, Antifungal, Anti-inflammatory, analgesic |
| Cannabichromevarinic acid (CBCVA) | $R_1 = COOH, R_2 = C_3H_7$ | |
| Cannabichromevarin (CBCV) | $R_1 = H, R_2 = C_3H_7$ | |

Cannabidiol class

| Cannabidiolic acid (CBDA) | $R_1 = COOH, R_2 = C_5H_{11}, R_3 = H$ | Antibiotic |
|---|---|---|
| Cannadidiol (CBD) | $R_1 = H, R_2 = C_5H_{11}, R_3 = H$ | Anxiolytic, Antipsychotic, Analgesisc, Anti-inflammatory, Antioxidant, antipasmodic |
| Cannabidiol monomethylether (CBDM) | $R_1 = H, R_2 = C_5H_{11}, R_3 = CH_3$ | |
| Cannabidiol-$C_4$ (CBD-$C_4$) | $R_1 = H, R_2 = C_4H_9, R_3 = H$ | |
| Cannabidivarinic acid (CBDVA) | $R_1 = COOH, R_2 = C_3H_7, R_3 = H$ | |
| Cannabidivarin (CBDV) | $R_1 = COOH, R_2 = C_3H_7, R_3 = H$ | |
| Cannabidiorcol (CBD-$C_1$) | $R_1 = H, R_2 = CH_3, R_3 = H$ | |

Delta-9-tetrahydrocannabinol class

| Delta-9-tetrahydrocannabinolic acid A (THCA-A) | $R_1 = COOH, R_2 = C_5H_{11}, R_3 = COOH$ | |
|---|---|---|
| Delta-9-tetrahydrocannabinolic acid A (THCA-B) | $R_1 = H, R_2 = C_5H_{11}, R_3 = COOH$ | |
| Delta-9-tetrahydrocannabinol (THC) | $R_1 = H, R_2 = C_5H_{11}, R_3 = H$ | Euphoriant, Analgesic, Anti-inflammatory, Antioxidant, Antiemetic |

TABLE 1-continued

| Compound | Structure | Main pharmacological characteristics |
|---|---|---|
| Delta-9-tetrahydrocannabinolic acid-$C_4$ (THCA-$C_4$) | $R_1$ = COOH, $R_2$ = $C_4H_9$, $R_3$ = H or $R_1$ = H, $R_2$ = $C_4H_9$, $R_3$ = COOH | |
| Delta-9-tetrahydrocannabinol-$C_4$ (THC-$C_4$) | $R_1$ = H, $R_2$ = $C_4H_9$, $R_3$ = H | |
| Delta-9-tetrahydrocannabivarinic acid-$C_4$ (THCV) | $R_1$ = H, $R_2$ = $C_3H_7$, $R_3$ = H | |
| Delta-8-tetrahydrocannabinol class | | |
| Delta-8-tetrahydrocannabinolic acid ($\Delta^8$- THCA) | 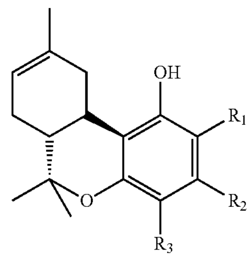 | |
| Delta-8-tetrahydrocannabinol ($\Delta^8$-THC) | $R_1$ = H, $R_2$ = $C_5H_{11}$ | Similar to THC (less potent) |

Methods of Growing Plants with Bioceramics

Recognized herein are methods for growing plants with a bioceramic. In some cases, the plant is a plant from the Cannabaceae family. In some cases the plant from the Cannabaceae family is a plant from the *Cannabis* genus. The *Cannabis* plant can be a *Cannabis sativa* plant, a *Cannabis indica* plant, or a hybrid plant of two or more *Cannabis* species. Recognized herein are compositions and methods that improve the growth of the Cannabaceae plants on a substrate. The substrate typically refers to a medium used to support the growth of the plant. The substrate can be a soil or a water solvent. The compositions typically refer to bioceramic compositions comprising tourmaline, kaolinite, and at least one additional oxide. In some instances the presence of the bioceramic comprising the kaolinite and the tourmaline on the substrate modulates a phytocannabinoid profile of the *Cannabis* plant, such as an amount of a tetrahydrocannabinol (THC) in the *Cannabis* plant, an amount of a Cannabidiol (CBD) in the *Cannabis* plant, or an amount of a delta-8- or delta-9-tetrahydrocannabinol, a cannabinol (CBN), a cannabicyclol (CBL), a cannabichromene (CBC), or a cannabigerol (CBG).

The bioceramic composition can be added to a substrate at all stages of plant growth. *Cannabis* plants go through a series of stages as they grow and mature. Different stages may require different amounts of light, nutrients, and water. These stages may also be associated with when to prune and train the plants. Generally, the life cycle of *cannabis* can be broken down into four primary stages from seed to harvest: germination, seedling, vegetative, and flowering.

Germination Stage: the first stage of life for a *cannabis* plant begins with the seed. Generally, a *cannabis* plant is dormant at the seed stage. Germination is the process in which a new plant begins to grow from a seed, and it typically requires water, heat, and air. A bioceramic of the disclosure can be added to a substrate, for example to a water or to a soil substrate at the seed of growth. This stage can last about 1 week, from about 1 week to about 2 weeks, or from about 1 week to about 3 weeks.

Seedling Stage: the second stage of life for a *cannabis* plant is seedling. Once a tap root has appeared and a seed has popped, the *Cannabis* plant is ready to be placed in a growing substrate. The growing substrate can comprise a bioceramic described herein. The tap root will drive down while the stem of the seedling will grow upwards. Initially, two rounded cotyledon leaves will grow from the stem as the plant unfolds from the protective casing of the seed. These initial leaves are responsible for taking in the sunlight needed for plant growth. As the roots develop, the first fan leaves grow, and at this point, the *Cannabis* plant can be considered a seedling. FIG. 1 illustrates a root system of a Cannabaceae plant, *Cannabis indica* grown in a soil substrate as described herein. This stage can last about 1 week, from about 1 week to about 2 weeks, or from about 1 week to about 3 weeks.

Vegetative Stage: *Cannabis* plants are considered seedlings until they begin to develop leaves with a full number of fingers on new fan leaves. The vegetative stage of *Cannabis* is where the plant's growth increases substantially. In some cases, the plant is transplanted into a different substrate, such as a larger pot, and the roots and foliage develop. This is also the time to begin topping or training the plants. This stage can last from about 1 week to about 8 weeks, from about 2 weeks to about 8 weeks, from about 3 weeks to about 8 weeks, from about 3 weeks to about 7 weeks, from about 3 weeks to about 6 weeks, from about 4 weeks to about 8 weeks, from about 4 weeks to about 7 weeks, or from about 4 weeks to about 6 weeks.

Flowering Stage: the flowering stage is the final stage of growth for the *Cannabis* plant. Flowering occurs naturally when the plant receives less than 12 hours of light a day as the summer days shorten (or as the light cycle indoors is reduced). It is in this stage that resinous buds develop.

In some instances, a bioceramic of the disclosure is added to one or more stages in the growth of a *Cannabis* plant. In some instances, the substrate comprises an amount of a kaolinite, a tourmaline, and at least one oxide selected from the group consisting of silicon dioxide ($SiO_2$), aluminum oxide ($Al_2O_3$), titanium dioxide ($TiO_2$), magnesium oxide (MgO), and Zirconium Oxide ($ZrO_2$). Additionally, some embodiments further comprise adding a second quantity of a kaolinite, a second quantity of a tourmaline, and optionally a second quantity of the aforementioned oxides to the substrate after a first period of time. The first period of time can be from 7 days to 80 days, from 20 days to 80 days, from 20 days to 60 days, or from 20 days to 40 days. The first period of time can be any time in the germination, seedling, vegetative, or flowering stages; or any time during the total life cycle of the plant.

Additionally, some embodiments further comprise adding a third quantity of a kaolinite and a third quantity of a tourmaline to the substrate to the substrate after a second period of time, and optionally a third quantity of at least one oxide selected from the group consisting of silicon dioxide ($SiO_2$), aluminum oxide ($Al_2O_3$), titanium dioxide ($TiO_2$), and magnesium oxide (MgO). The second period of time can be from 7 days to 160 days, from 20 days to 160 days, from 20 days to 140 days, from 20 days to 120 days, from 20 days to 100 days, from 20 days to 80 days, from 20 days to 60 days, from 20 days to 40 days after the first period of time. The second period of time can be any time in the germination, seedling, vegetative, or flowering stages; or any time during the total life cycle of the plant.

Soil Substrates

As used herein a soil generally refers to a mixture of organic matter, liquids, minerals, gases, organisms, and frequently microorganisms. Soils perform a number of functions in supporting plant growth, including helping plants absorb water, adjusting soil pH, and providing nutrients to plants. Of all of the minerals found in soil, nitrogen, phosphorous, and potassium are the three most important that plants actively extract from the soil as nutrients. Correcting soil mineral content is an important part of raising healthy plants. For example, molds are fungi that can be found both indoors and outdoors. Fungus spores generally attach to a young plant leaf where they are able to germinate and grow, quickly spreading to other parts of the plant and nearby plants. Both indoor and outdoor plants are susceptible to infection, especially in warm, humid areas. In most cases, the mold will not kill an established plant, but it can weaken the plant and reduce the output of vegetation, as well as spread to other plants. In some instances, a bioceramic of the disclosure can help reduce an amount of mold spores on a plant or it can help reduce the growth of mold spores on the plant.

Various soils can be used as suitable substrates for the growth of a plant described herein. The soil substrate can comprise an amount of essential and non-essential nutrients. The soil substrate can comprises less than 10% dry weight, less than 15% dry weight, less than 20% dry weight, less than 25% dry weight, less than 30% dry weight, less than 35% dry weight, less than 40% dry weight, less than 50% dry weight, or another suitable amount of essential minerals such as of nitrogen (N), phosphorus (P), potassium (K), calcium (Ca), sulfur (S), magnesium (Mg), and sodium (Na). The substrate can comprises less than 0.01% dry weight, less than 0.1% dry weight, less than 0.5% dry weight, less than 1% dry weight, or another suitable amount of one or more trace minerals selected from the group consisting of: boron (B), chlorine (Cl), manganese (Mn), iron (Fe), zinc (Zn), copper (Cu), molybdenum (Mo), nickel (Ni), and cobalt (Co).

A soil substrate as used herein can be a cemented soil. A cemented soil comprises a soil in which the particles are held together by a chemical agent, such as calcium carbonate, such that a hand-size sample cannot be crushed into powder or individual soil particles by finger pressure.

A soil substrate as used herein can be a cohesive soil. A cohesive soil comprises a clay (fine grained soil), or soil with a high clay content, which has cohesive strength. A cohesive soil does not crumble, can be excavated with vertical sideslopes, and is plastic when moist. A cohesive soil is hard to break up when dry, and exhibits significant cohesion when submerged. Cohesive soils include clayey silt, sandy clay, silty clay, clay and organic clay.

A soil substrate as used herein can be a granular soil. A granular soil comprises gravel, sand, or silt (coarse grained soil) with little or no clay content. A granular soil has no cohesive strength. Some moist granular soils exhibit apparent cohesion, however they cannot be molded when moist and crumble easily when dry.

A soil substrate as used herein can be a layered system soil. As used herein, a layered system soil means two or more distinctly different soil or rock types arranged in layers. Micaceous seams or weakened planes in rock or shale are non-limiting examples of layered soil systems.

A soil substrate as used herein can be a moist soil. A moist soil comprises a condition in which a soil looks and feels damp. Moist cohesive soils can easily be shaped into a ball and rolled into small diameter threads before crumbling. Moist granular soil that contains some cohesive material will exhibit signs of cohesion between particles.

The soil substrates described herein can be plastic. As used herein "plastic" means a property of a soil which allows the soil to be deformed or molded without cracking, or appreciable volume change.

As used herein a "saturated soil" generally refers to a soil in which the voids are filled with water.

Water Substrates or Solvents

Hydroponics is a method of growing plants without using soil (i.e., soil less, in an inert physical support, or with minimum use of soil). This technique instead uses a mineral nutrient solution in a water solvent, allowing the nutrient uptake process to be more efficient than when using soil. Various types of water solvents or hydroponic systems can be used as suitable substrates for the growth of a plant described herein. The water substrate can comprise an amount of essential and non-essential nutrients. A water solvent can be used, for example, in the hydroponics process of growing plants in sand, gravel, or liquid, with added nutrients but without soil. The substrate can comprises less than 10% dry weight, less than 15% dry weight, less than 20% dry weight, less than 25% dry weight, less than 30% dry weight, less than 35% dry weight, less than 40% dry weight, less than 50% dry weight, or another suitable amount of essential minerals such as of nitrogen (N), phosphorus (P), potassium (K), calcium (Ca), sulfur (S), magnesium (Mg), and sodium (Na). The substrate can comprises less than 0.01% dry weight, less than 0.1% dry weight, less than 0.5% dry weight, less than 1% dry weight, or another suitable amount of one or more trace minerals selected from the group consisting of: boron (B), chlorine (Cl), manganese (Mn), iron (Fe), zinc (Zn), copper (Cu), molybdenum (Mo), nickel (Ni), and cobalt (Co).

Unlike plants grown in soil, plants grown in a hydroponics system do not need to develop extensive root structures to search for nutrients. In the hydroponics method, plants are raised in an inert growing medium where the plants only need to expend minimal energy to acquire nutrients from the roots. Furthermore, it is easier to test and adjust pH levels. The energy saved by the roots is better spent on fruit and flower production. There are several types of hydroponic growing techniques, including: Nutrient film technique (NFT), wicks system, Ebb and flow (flood and drain), Water culture, drip system, and aeroponic system.

The nutrient film technique (NFT) is a hydroponic growing technique where a small, shallow stream of nutrient-rich water is recirculated over roots through a channel, gutter, or tube. NFT can be similar to the ebb and flow system in that it utilizes a pump to move nutrients in a continuous, constant flow. The difference with NFT is that the solution flows directly over the roots.

A wick system generally refers to a watering method for potted plants that uses a soft fabric string known as a wick. One end of the wick is buried in the soil, and the other end hangs into a pot, dish, or bucket of water. Water will flow up the wick and water the plant until the soil surrounding the plant is damp. Once the soil dries out, the wick will again soak up water.

Deep water culture generally refers to a type of hydroponic system in which the plant's roots are submerged in a growth-inducing mixture containing essential nutrients and minerals. In this system the plants are aerated via an air pump. Some plants, such as lettuce, thrive in water and are commonly grown using deep water culture.

Drip systems generally refer to systems having one or more drip emitters that drip a mix of water and nutrient solution onto the surface of the grow media, rather than spraying it on or washing it over the roots in larger quantities. Drip systems can be set up using grow containers, where each plant has its own pot to sit in and has its own emitter, or in grow beds, where the plants all share the same root zone area.

Aeroponics is an indoor gardening practice in which plants are grown and nourished by suspending their root structures in air and regularly spraying them with a nutrient and water solution. Soil is not used for aeroponics, because the plants can thrive when their roots are constantly or periodically exposed to a nutrient-rich mist. Aeroponics offers an efficient means to grow plants, including fruits and vegetables, without potting and repotting them to replenish their access to nutrient-rich soil.

Aquaponics generally refers to the combination of aquaculture, i.e., raising fish, and hydroponics to yield a method for growing fish and plants together in one integrated system. In some instances, the fish waste can provide an organic food source for the plants, and the plants can naturally filter the water for the fish. Aquaponics methods may also include the presence of microbes (nitrifying bacteria). These bacteria can convert ammonia from the fish waste first into nitrites, and then into nitrates.

Substrates Comprising Kaolinite, Tourmaline, and Oxides

Recognized herein are methods for growing plants from the Cannabaceae family on a substrate, the method comprising: cultivating the plant from the Cannabaceae family on the substrate, wherein the substrate comprises at most 1 part volume of a bioceramic composition to 18 parts volume of the substrate. The bioceramic composition can comprise an amount of kaolinite, tourmaline, and at least one additional oxide. In some cases, the at least one oxide is selected from the group consisting of silicon dioxide ($SiO_2$), aluminum oxide ($Al_2O_3$), titanium dioxide ($TiO_2$), magnesium oxide (MgO), and zirconium dioxide ($ZrO_2$).

In some instances, the bioceramic formulations described herein generally comprise from about 20 wt % to about 80 wt % kaolinite ($Al_2Si_2O_5(OH)_4$), from about 1 wt % to about 30 wt % tourmaline, and at least one additional oxide up to 100 wt % of a total weight of the bioceramic composition.

In some instances, the bioceramic composition comprises from about 40 wt % to about 60 wt % kaolinite ($Al_2Si_2O_5(OH)_4$) to about 5 wt % to about 15 wt % tourmaline to about 15 wt % to about 25 wt % aluminum oxide ($Al_2O_3$) to about 10 wt % to about 20 wt % silicon dioxide ($SiO_2$); and from about 1 wt % to about 20 wt % titanium dioxide ($TiO_2$); by total weight of the composition.

In some instances, the disclosed bioceramics can be added to a substrate in a volume-to-volume ratio. In some embodiments, a bioceramic composition of the disclosure is mixed at a ratio of at most 1 part volume bioceramic to at most 1 part volume substrate, at most 1 part volume bioceramic composition to at most 2 parts substrate, at most 1 parts bioceramic to at most 3 parts substrate, at most 1 part volume bioceramic to at most 4 parts substrate, at most 1 part volume bioceramic to at most 5 parts substrate, at most 1 part volume bioceramic to at most 6 parts substrate, at most 1 part volume bioceramic to at most 7 parts substrate, at most 1 part volume bioceramic to at most 8 parts substrate, at most 1 part volume bioceramic to at most 9 parts substrate, at most 1 part volume bioceramic to at most 10 parts substrate, at most 1 part volume bioceramic to at most 11 parts substrate, at most 1 part volume bioceramic to at most 12 parts substrate, at most 1 part volume bioceramic to at most 13 parts substrate, at most 1 part volume bioceramic to at most 14 parts substrate, at most 1 part volume bioceramic to at most 15 parts substrate, at most 1 part volume bioceramic to at most 16 parts substrate, at most 1 part volume bioceramic to at most 17 parts substrate, at most 1 part volume bioceramic to at most 18 parts substrate, at most 1 part volume bioceramic to at most 19 parts substrate, at most 1 part volume bioceramic to at most 20 parts substrate, at most 1 part volume bioceramic to at most 21 parts substrate, at most 1 part volume bioceramic to at most 22 parts substrate, at most 1 part volume bioceramic to at most 23 parts substrate, at most 1 part volume bioceramic to at most 24 parts substrate, at most 1 part volume bioceramic to at most 25 parts substrate, at most 1 part volume bioceramic to at most 26 parts substrate, at most 1 part volume bioceramic to at most 27 parts substrate, at most 1 part volume bioceramic to at most 28 parts substrate, at most 1 part volume bioceramic to at most 29 parts substrate, at most 1 part volume bioceramic to at most 30 parts substrate, at most 1 part volume bioceramic to at most 31 parts substrate, at most 1 part volume bioceramic to at most 32 parts substrate, at most 1 part volume bioceramic to at most 33 parts substrate, at most 1 part volume bioceramic to at most 34 parts substrate, at most 1 part volume bioceramic to at most 35 parts substrate, at most 1 part volume bioceramic to at most 36 parts substrate, at most 1 part volume bioceramic to at most 37 parts substrate, at most 1 part volume bioceramic to at most 38 parts substrate, at most 1 part volume bioceramic to at most 39 parts substrate, at most 1 part volume bioceramic to at most 40 parts substrate, at most 1 part volume bioceramic to at most 41 parts substrate, at most 1 part volume bioceramic to at most 42 parts substrate, at most 1 part volume bioceramic to at most 43 parts substrate, at most 1 part volume bioceramic to at most 44 parts substrate, at most 1 part volume bioceramic to at most 45 parts substrate, at most 1 part volume bioceramic to at most 46 parts substrate, at most 1 part volume bioceramic to at most 47 parts substrate, at most 1 part volume bioceramic to at most 48 parts substrate, at most 1 part volume bioceramic to at most 49 parts substrate, at most 1 part volume bioceramic to at most 50 parts substrate, at most 1 part volume bioceramic to at most 51 parts substrate, at most 1 part volume bioceramic to at most 52 parts substrate, at most 1 part volume bioceramic to at most 53 parts substrate, at most 1 part volume bioceramic to at most 54 parts substrate, at most 1 part volume bioceramic to at most 55 parts substrate, at most 1 part volume bioceramic to at most 56 parts substrate, at most 1 part volume bioceramic to at most 57 parts substrate, at most 1 part volume bioceramic to at most 58 parts substrate, at most 1 part volume bioceramic to at most 59 parts substrate, at most 1 part volume bioceramic to at most 60 parts substrate, at most 1 part volume bioceramic to at most 61 parts substrate, at most 1 part volume bioceramic to at most 62 parts substrate, at most 1 part volume bioceramic to at most 63 parts substrate, at most 1 part volume bioceramic to at most 64 parts substrate, at most 1 part volume bioceramic to at most 65 parts substrate, at most 1 part volume bioceramic to at most 66 parts substrate, at most 1 part volume bioceramic to at most 67 parts substrate, at most 1 part volume bioceramic to at most 68 parts substrate, at most 1 part volume bioceramic to at most 69 parts substrate, at most 1 part volume bioceramic to at most 70 parts substrate, at most 1 part volume bioceramic to at most 71 parts substrate, at most 1 part volume bioceramic to at most 72 parts substrate, at most 1 part volume bioceramic to at most 73 parts substrate, at most 1 part volume bioceramic to at most 74 parts substrate, at most 1 part volume bioceramic to at most 75 parts substrate, at most 1 part volume bioceramic to at most 76 parts substrate, at most 1 part volume bioceramic to at most 77 parts substrate, at most 1 part volume bioceramic to at most 78 parts substrate, at most 1 part volume bioceramic to at most 79 parts substrate, at most 1 part volume bioceramic to at most 80 parts substrate, at most 1 part volume bioceramic to at most 81 parts substrate, at most 1 part volume bioceramic to at most 82 parts substrate, at most 1 part volume bioceramic to at most 83 parts substrate, at most 1 part volume bioceramic to at most 84 parts substrate, at most 1 part volume bioceramic to at most 85 parts substrate, at most 1 part volume bioceramic to at most 86 parts substrate, at most 1 part volume bioceramic to at most 87 parts substrate, at most 1 part volume bioceramic to at most 88 parts substrate, at most 1 part volume bioceramic to at most 89 parts substrate, at most 1 part volume bioceramic to at most 90 parts substrate, at most 1 part volume bioceramic to at most 91 parts substrate, at most 1 part volume bioceramic to at most 92 parts substrate, at most 1 part volume bioceramic to at most 93 parts substrate, at most 1 part volume bioceramic to at most 94 parts substrate, at most 1 part volume bioceramic to at most 95 parts substrate, at most 1 part volume bioceramic to at most 96 parts substrate, at most 1 part volume bioceramic to at most 97 parts substrate, at most 1 part volume bioceramic to at most 98 parts substrate, at most 1 part volume bioceramic to at most 99 parts substrate, or at most 1 part volume bioceramic to at most 100 parts substrate, or another suitable ratio where the substrate is a soil or a water solvent.

In some embodiments, a bioceramic composition of the disclosure is mixed at a ratio of from about 1 part volume bioceramic to about 1 part volume substrate, from about 1 part volume bioceramic to about 2 parts substrate, from about 1 parts bioceramic to about 3 parts substrate, from about 1 part volume bioceramic to about 4 parts substrate, from about 1 part volume bioceramic to about 5 parts substrate, from about 1 part volume bioceramic to about 6 parts substrate, from about 1 part volume bioceramic to about 7 parts substrate, from about 1 part volume bioceramic to about 8 parts substrate, from about 1 part volume bioceramic to about 9 parts substrate, from about 1 part volume bioceramic to about 10 parts substrate, from about 1 part volume bioceramic to about 11 parts substrate, from about 1 part volume bioceramic to about 12 parts substrate, from about 1 part volume bioceramic to about 13 parts substrate, from about 1 part volume bioceramic to about 14 parts substrate, from about 1 part volume bioceramic to about 15 parts substrate, from about 1 part volume bioceramic to about 16 parts substrate, from about 1 part volume bioceramic to about 17 parts substrate, from about 1 part volume bioceramic to about 18 parts substrate, from about 1 part volume bioceramic to about 19 parts substrate, from about 1 part volume bioceramic to about 20 parts substrate, from about 1 part volume bioceramic to about 21 parts substrate, from about 1 part volume bioceramic to about 22 parts substrate, from about 1 part volume bioceramic to about 23 parts substrate, from about 1 part volume bioceramic to about 24 parts substrate, from about 1 part volume bioceramic to about 25 parts substrate, from about 1 part volume bioceramic to about 26 parts substrate, from about 1 part volume bioceramic to about 27 parts substrate, from about 1 part volume bioceramic to about 28 parts substrate, from about 1 part volume bioceramic to about 29 parts substrate, from about 1 part volume bioceramic to about 30 parts substrate, from about 1 part volume bioceramic to about 31 parts substrate, from about 1 part volume bioceramic to about 32 parts substrate, from about 1 part volume bioceramic to about 33 parts substrate, from about 1 part volume bioceramic to about 34 parts substrate, from about 1 part volume bioceramic to about 35 parts substrate, from about 1 part volume bioceramic to about 36 parts substrate, from about 1 part volume bioceramic to about 37 parts substrate, from about 1 part volume bioceramic to about 38 parts substrate, from about 1 part volume bioceramic to about 39 parts substrate, from about 1 part volume bioceramic to about 40 parts substrate, from about 1 part volume bioceramic to about 41 parts substrate, from about 1 part volume bioceramic to about 42 parts substrate, from about 1 part volume bioceramic to about 43 parts substrate, from about 1 part volume bioceramic to about 44 parts substrate, from about 1 part volume bioceramic to about 45 parts substrate, from about 1 part volume bioceramic to about 46 parts substrate, from about 1 part volume bioceramic to about 47 parts substrate, from about 1 part volume bioceramic to about 48 parts substrate, from about 1 part volume bioceramic to about 49 parts substrate, from about 1 part volume bioceramic to about 50 parts substrate, from about 1 part volume bioceramic to about 51 parts substrate, from about 1 part volume bioceramic to about 52 parts substrate, from about 1 part volume bioceramic to about 53 parts substrate, from about 1 part volume bioceramic to about 54 parts substrate, from about 1 part volume bioceramic to about 55 parts substrate, from about 1 part volume bioceramic to about 56 parts substrate, from about 1 part volume bioceramic to about 57 parts substrate, from about 1 part volume bioceramic to about 58 parts substrate, from about 1 part volume bioceramic to about 59 parts substrate, from about 1 part volume bioceramic to about 60 parts substrate, from about 1 part volume bioceramic to about 61 parts substrate, from about 1 part volume bioceramic to about 62 parts substrate, from about 1 part volume bioceramic to about 63 parts substrate, from about 1 part volume bioceramic to about 64 parts substrate, from about 1 part volume bioceramic to about 65 parts substrate, from about 1 part volume bioceramic to about 66 parts substrate, from about 1 part volume bioceramic to about 67 parts substrate, from about 1 part volume bioceramic to about 68 parts substrate, from about 1 part volume bioceramic to about 69 parts substrate, from about 1 part volume bioceramic to about 70 parts substrate, from about 1 part volume bioceramic to about 71 parts substrate, from about 1 part volume bioceramic to about 72 parts substrate, from about 1 part volume bioceramic to about 73 parts substrate, from about 1 part volume bioceramic to about 74 parts substrate, from about 1 part volume bioceramic to about 75 parts substrate, from about 1 part volume bioceramic to about 76 parts substrate, from about 1 part volume bioceramic to about 77 parts substrate, from about 1 part volume bioceramic to about 78 parts substrate, from about 1 part volume bioceramic to about 79 parts substrate, from about 1 part volume bioceramic to about 80 parts substrate, from about 1 part volume bioceramic to about 81 parts substrate, from about 1 part volume bioceramic to about 82 parts substrate, from about 1 part volume bioceramic to about 83 parts substrate, from about 1 part volume bioceramic to about 84 parts substrate, from about 1 part volume bioceramic to about 85 parts substrate, from about 1 part volume bioceramic to about 86 parts substrate, from about 1 part volume bioceramic to about 87 parts substrate, from about 1 part volume bioceramic to about 88 parts substrate, from about 1 part volume bioceramic to about 89 parts substrate, from about 1 part volume bioceramic to about 90 parts substrate, from about 1 part volume bioceramic to about 91 parts substrate, from about 1 part volume bioceramic to about 92 parts substrate, from about 1 part volume bioceramic to about 93 parts substrate, from about 1 part volume bioceramic to about 94 parts substrate, from about 1 part volume bioceramic to about 95 parts substrate, from about 1 part volume bioceramic to about 96 parts substrate, from about 1 part volume bioceramic to about 97 parts substrate, from about 1 part volume bioceramic to about 98 parts substrate, from about 1 part volume bioceramic to about 99 parts substrate, or from about 1 part volume bioceramic to about 100 parts substrate, or another suitable ratio where the substrate is a soil or a water solvent.

Recognized herein are methods for growing plants from the Cannabaceae family on a substrate, the method comprising: cultivating the plant from the Cannabaceae family on the substrate, wherein the substrate comprises: a) at most 1 part of a kaolinite to 18 parts of the substrate; and b) at most 1 part of a tourmaline to 18 parts of the substrate. In some cases, the substrate comprises at most 1 part per volume of a kaolinite to 18 parts per volume of the substrate, at most 1 part per weight of a kaolinite to 18 parts per weight of the substrate, at most 1 part per weight of a kaolinite to 18 parts per volume of the substrate, or at most 1 part per volume of a kaolinite to 18 parts per weight of a substrate. In some cases, the substrate comprises at most 1 part per volume of a tourmaline to 18 parts per volume of the substrate, the substrate comprises at most 1 part per weight of a tourmaline to 18 parts per weight of the substrate, at most 1 part per weight of a tourmaline to 18 parts per volume of the substrate, or at most 1 part per volume of a tourmaline to 18 parts per weight of a substrate.

As used herein, the term "tourmaline" retains its meaning known in the mineral and gemstone arts. For example, tourmaline is a group of isomorphous minerals with an identical crystal lattice. Each member of the tourmaline group has its own chemical formula, due to small differences in their elemental distribution. For example, in some embodiments, the tourmaline has the following generic formula $X_1Y_3Al_6(BO_3)_3Si_6O_{18}(OH)_4$, where: X=Na and/or Ca and Y=Mg, Li, Al, and/or $Fe^{2+}$ which is represented with the following formula, $(Na,Ca)(Mg,Li,Al,Fe^{2+})_3Al_6(BO_3)_3Si_6O_{18}(OH)_4$.

In some embodiments, the Al may be replaced by other elements. For example, in Uvite, the Al is partially replaced by Mg which expands the formula to: $(Na,Ca)(Mg,Li,Al,Fe^{2+})_3(Al,Mg,Cr)_6(BO_3)_3Si_6O_{18}(OH)_4$.

In some embodiments, the tourmaline is Buergerite which contains three O atoms and one F atom in place of the OH radical. A Buergerite molecule also contains an Fe atom that is in a 3+ oxidation state which is depicted as: $(Na,Ca)(Mg,Li,Al,Fe^{2+},Fe^{3+})_3(Al,Mg,Cr)_6(BO_3)_3Si_6O_{18}(OH_2O,F)_4$. In other embodiments, the tourmaline is one or more of the following:

Schorl: $NaFe^{2+}_3Al_6(BO_3)_3Si_6O_{18}(OH)_4$;
Dravite: $NaMg_3Al_6(BO_3)_3Si_6O_{18}(OH)_4$;
Elbaite: $Na(Li,Al)_3Al_6(BO_3)_3Si_6O_{18}(OH)_4$;
Liddicoatite: $Ca(Li,Al)_3Al_6(BO_3)_3Si_6O_{18}(OH)_4$;
Uvite: $Ca(Mg,Fe^{2+})_3Al_5Mg(BO_3)_3Si_6O_{18}(OH)_4$;
Buergerite: $NaFe^{3+}_3Al_6(BO_3)_3Si_6O_{18}O_3F$.

In one embodiment, the bioceramic composition tourmaline that comprises $NaFe^{2+}_3Al_6Si_6O_{18}(BO_3)_3(OH)_3OH$.

Another aspect of the methods and compositions described herein is a bioceramic composition of micrometer particle size. For example, in some embodiments, provided is a bioceramic composition containing a largest dimension of any particle in the bioceramic of from about 0.1 micrometer ($\mu m$) to about 250 micrometers. In further or additional embodiments, provided is a bioceramic composition that can be formulated into a powder or another product disclosed herein provided that the largest dimension of any particle in the bioceramic is from about 0.5 micrometers to about 25 micrometers. In some cases, a bioceramic particle can have a diameter, or cross-sectional area, of about 0.1 $\mu m$ to about 1 $\mu m$, of about 0.1 $\mu m$ to about 10 $\mu m$, of about 0.1 $\mu m$ to about 20 $\mu m$, of about 0.1 $\mu m$ to about 30 $\mu m$, of about 0.1 $\mu m$ to about 40 $\mu m$, of about 0.1 $\mu m$ to about 50 $\mu m$, of about 0.1 $\mu m$ to about 60 $\mu m$, of about 0.1 $\mu m$ to about 70 $\mu m$, of about 0.1 $\mu m$ to about 80 $\mu m$, of about 0.1 $\mu m$ to about 90 $\mu m$, of about 0.1 $\mu m$ to about 100 $\mu m$, or other desired size. In some cases, an inlet can have a cross-sectional diameter of about 10 $\mu m$ to about 100 $\mu m$, of about 10 $\mu m$ to about 200 $\mu m$, of about 10 $\mu m$ to about 300 $\mu m$, of about 10 $\mu m$ to about 400 $\mu m$, of about 10 $\mu m$ to about 500 $\mu m$, or other desired size.

Kaolinite is a layered silicate mineral comprising oxides. In some cases, various oxides are comprised within the kaolinite. In some cases, a bioceramic composition comprises additional oxides that are not part of the kaolinite. In some embodiments, a bioceramic composition comprises one oxide, two oxides, three oxides, four oxides, five oxides, six oxides, seven oxides, eight oxides, nine oxides, ten oxides, eleven oxides, twelve oxides, or more oxides. In some cases, the additional oxides are highly refractory oxides.

In some embodiments, an oxide of a bioceramic composition of matter of the disclosure has various oxidation states. An oxide of the disclosure has an oxidation number of +1, +2, +3, +4, +5, +6, +7, or +8. In some cases a bioceramic composition of the disclosure will have more than one oxide wherein at least one oxide has a different oxidation number as compared to the other oxide. For example, in some cases a bioceramic composition of the disclosure comprises an aluminum oxide ($Al_2O_3$) with a +2 or a +3 oxidation state, a silicon dioxide ($SiO_2$) with a +4 oxidation state, and a zirconium oxide ($ZrO_2$) with a +4 oxidation state.

Non-limiting examples of oxides with +1 oxidation state include: copper(I) oxide ($Cu_2O$), dicarbon monoxide ($C_2O$), dichlorine monoxide ($Cl_2O$), lithium oxide ($Li_2O$), potassium oxide ($K_2O$), rubidium oxide ($Rb_2O$), silver oxide ($Ag_2O$), thallium(I) oxide ($Tl_2O$), sodium oxide ($Na_2O$), or water (Hydrogen oxide) ($H_2O$).

Non-limiting examples of oxides with +2 oxidation state include: aluminium(II) oxide (AlO), barium oxide (BaO), beryllium oxide (BeO), cadmium oxide (CdO), calcium oxide (CaO), carbon monoxide (CO), chromium(II) oxide (CrO), cobalt(II) oxide (CoO), copper(II) oxide (CuO), iron(II) oxide (FeO), lead(II) oxide (PbO), magnesium oxide (MgO), mercury(II) oxide (HgO), nickel(II) oxide (NiO), nitric oxide (NO), palladium(II) oxide (PdO), strontium oxide (SrO), sulfur monoxide (SO), disulfur dioxide ($S_2O_2$), tin(II) oxide (SnO), titanium(II) oxide (TiO), vanadium(II) oxide (VO), or zinc oxide (ZnO).

Non-limiting examples of oxides with +3 oxidation states include: aluminium oxide ($Al_2O_3$), antimony trioxide ($Sb_2O_3$), arsenic trioxide ($As_2O_3$), bismuth(III) oxide ($Bi_2O_3$), boron trioxide ($B_2O_3$), chromium(III) oxide ($Cr_2O_3$), dinitrogen trioxide ($N_2O_3$), erbium(III) oxide ($Er_2O_3$), gadolinium(III) oxide ($Gd_2O_3$), gallium(III) oxide ($Ga_2O_3$), holmium(III) oxide ($Ho_2O_3$), indium(III) oxide ($In_2O_3$), iron(III) oxide ($Fe_2O_3$), lanthanum oxide ($La_2O_3$), lutetium(III) oxide ($Lu_2O_3$), nickel(III) oxide ($Ni_2O_3$), phosphorus trioxide ($P_4O_6$), promethium(III) oxide ($Pm_2O_3$), rhodium(III) oxide ($Rh_2O_3$), samarium(III) oxide ($Sm_2O_3$), scandium oxide ($Sc_2O_3$), terbium(III) oxide ($Tb_2O_3$), thallium(III) oxide ($Tl_2O_3$), thulium(III) oxide ($Tm_2O_3$), titanium(III) oxide ($Ti_2O_3$), tungsten(III) oxide ($W_2O_3$), vanadium(III) oxide ($V_2O_3$), ytterbium(III) oxide ($Yb_2O_3$), yttrium (III) oxide ($Y_2O_3$).

Non-limiting examples of oxides with +4 oxidation states include: carbon dioxide ($CO_2$), carbon trioxide ($CO_3$), cerium(IV) oxide ($CeO_2$), chlorine dioxide ($ClO_2$), chromium (IV) oxide ($CrO_2$), dinitrogen tetroxide ($N_2O_4$), germanium dioxide ($GeO_2$), hafnium(IV) oxide ($HfO_2$), lead dioxide ($PbO_2$), manganese dioxide ($MnO_2$), nitrogen dioxide ($NO_2$), plutonium(IV) oxide ($PuO_2$), rhodium(IV) oxide ($RhO_2$), ruthenium(IV) oxide ($RuO_2$), selenium dioxide ($SeO_2$), silicon dioxide ($SiO_2$), sulfur dioxide ($SO_2$), tellurium dioxide ($TeO_2$), thorium dioxide ($ThO_2$), tin dioxide ($SnO_2$), titanium dioxide ($TiO_2$), tungsten(IV) oxide ($WO_2$), uranium dioxide ($UO_2$), vanadium(IV) oxide ($VO_2$), or zirconium dioxide ($ZrO_2$).

Non-limiting examples of oxides with +5 oxidation states include: antimony pentoxide ($Sb_2O_5$), arsenic pentoxide ($As_2O_5$), dinitrogen pentoxide ($N_2O_5$), niobium pentoxide ($Nb_2O_5$), phosphorus pentoxide ($P_2O_5$), tantalum pentoxide ($Ta_2O_5$), or vanadium(V) oxide ($V_2O_5$). Non-limiting examples of oxides with +6 oxidation states include: chromium trioxide ($CrO_3$), molybdenum trioxide ($MoO_3$), rhenium trioxide ($ReO_3$), selenium trioxide ($SeO_3$), sulfur trioxide ($SO_3$), tellurium trioxide ($TeO_3$), tungsten trioxide ($WO_3$), uranium trioxide ($UO_3$), or xenon trioxide ($XeO_3$).

Non-limiting examples of oxides with +7 oxidation states include: dichlorine heptoxide ($Cl_2O_7$), manganese heptoxide ($Mn_2O_7$), rhenium(VII) oxide ($Re_2O_7$), or technetium(VII) oxide ($Tc_2O_7$). Non-limiting examples of oxides with +8 oxidation states include: osmium tetroxide ($OsO_4$), ruthenium tetroxide ($RuO_4$), xenon tetroxide ($XeO_4$), iridium tetroxide ($IrO_4$), or hassium tetroxide ($HsO_4$). Non-limiting examples of oxides with various states of oxidation include antimony tetroxide ($Sb_2O_4$), cobalt(II,III) oxide ($Co_3O_4$), iron(II,III) oxide ($Fe_3O_4$), lead(II,IV) oxide ($Pb_3O_4$), manganese(II,III) oxide ($Mn_3O_4$), or silver(I,III) oxide (AgO).

In further or additional embodiments a bioceramic composition of matter of the disclosure further comprises a metal. A metal can be in elemental form, such as a metal atom, or a metal ion. Non-limiting examples of metals include transition metals, main group metals, and metals of Group 3, Group 4, Group 5, Group 6, Group 7, Group 8, Group 9, Group 10, Group 11, Group 12, Group 13, Group 14, and Group 15 of the Periodic Table. Non-limiting examples of metal include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, tin, lead, and bismuth.

The proportion of minerals and oxides in a bioceramic composition can optionally be altered depending on a number of variables, including, for example, the amount of thermal radiation, more specifically far infrared radiation, to be emitted, or the Cannabaceae plant being cultivated.

Far-Infrared Emittance, Transmission, and Reflection

Yet another aspect of the methods and compositions described herein is a bioceramic composition that emits, transmits, and/or reflects an infrared wavelength in a substrate. In some embodiments, provided is a bioceramic that absorbs, stores, and/or reflects thermal energy, such as far infrared energy or rays. In some embodiments, provided is a bioceramic that emits, transmits, or reflects an infrared wavelength that is far infrared and that comprises a wavelength from about 1 micrometer to about 1 millimeter. In further or additional embodiments, provided is a bioceramic composition that emits, transmits, or reflects an infrared wavelength that is from about 3 micrometers to about 15 micrometers. In further or additional embodiments, described herein is a bioceramic composition that provides a reflectance of the bioceramic at a room temperature of 25° C. is at least 80% in an infrared range between about 7 micrometers and about 12 micrometers.

In some cases, a bioceramic of the disclosure can provide at most 1.5 joules/$cm^2$, at most 2 joules/$cm^2$, at most 3 joules/$cm^2$, at most 4 joules/$cm^2$, at most 5 joules/$cm^2$, at most 6 joules/$cm^2$, at most 7 joules/$cm^2$, at most 8 joules/$cm^2$, at most 9 joules/$cm^2$, at most 10 joules/$cm^2$, at most 11 joules/$cm^2$, at most 12 joules/$cm^2$, at most 13 joules/$cm^2$, at most 14 joules/$cm^2$, at most 15 joules/$cm^2$, at most 16 joules/$cm^2$, at most 17 joules/$cm^2$, at most 18 joules/$cm^2$, at most 19 joules/$cm^2$, at most 20 joules/$cm^2$, at most 21 joules/$cm^2$, at most 22 joules/$cm^2$, at most 23 joules/$cm^2$, at most 24 joules/$cm^2$, at most 25 joules/$cm^2$, at most 26 joules/$cm^2$, at most 27 joules/$cm^2$, at most 28 joules/$cm^2$, at most 29 joules/$cm^2$, at most 30 joules/$cm^2$, at most 31 joules/$cm^2$, at most 32 joules/$cm^2$, at most 33 joules/$cm^2$, at most 34 joules/$cm^2$, at most 35 joules/$cm^2$, at most 36 joules/$cm^2$, at most 37 joules/$cm^2$, at most 38 joules/$cm^2$, at most 39 joules/$cm^2$, at most 40 joules/$cm^2$, at most 41 joules/$cm^2$, at most 42 joules/$cm^2$, at most 43 joules/$cm^2$, at most 44 joules/$cm^2$, or at most 45 joules/$cm^2$ of far infrared energy or rays to a Cannabaceae plant.

In some cases, a method or bioceramic of the disclosure provides between 1.5 joules/$cm^2$ and 45 joules/$cm^2$, between 1.5 joules/$cm^2$ and 40 joules/$cm^2$, between 1.5 joules/$cm^2$ and 35 joules/$cm^2$, between 1.5 joules/$cm^2$ and 30 joules/$cm^2$, between 1.5 joules/$cm^2$ and 25 joules/$cm^2$, between 1.5 joules/$cm^2$ and 20 joules/$cm^2$, between 1.5 joules/$cm^2$ and 15 joules/$cm^2$, between 1.5 joules/$cm^2$ and 10 joules/$cm^2$, between 1.5 joules/$cm^2$ and 5 joules/$cm^2$, between 2 joules/$cm^2$ and 45 joules/$cm^2$, between 2 joules/$cm^2$ and 40 joules/$cm^2$, between 2 joules/$cm^2$ and 35 joules/$cm^2$, between 2 joules/$cm^2$ and 30 joules/$cm^2$, between 2 joules/$cm^2$ and 25 joules/$cm^2$, between 2 joules/$cm^2$ and 20 joules/$cm^2$, between 2 joules/$cm^2$ and 15 joules/$cm^2$, between 2 joules/ cm² and 10 joules/cm², between 2 joules/cm² and 5 joules/cm² of far infrared energy or rays to a Cannabaceae plant.

Medicinal Formulations

In an aspect of the instant disclosure, medicinal formulations comprise at least a portion of the Cannabaceae plant grown with the methods described herein. In some cases, the at least a portion of the Cannabaceae plant comprises a leave, a flower, a steam, or a seed. In some cases, the plant from the Cannabaceae family is a plant from the *Cannabis* genus, such as a *Cannabis sativa* plant, a *Cannabis indica* plant, or a hybrid plant of two or more *Cannabis* species.

A pharmaceutical composition of the disclosure can provide a therapeutically-effective amount of one or more cannabinoids. A pharmaceutical composition of the disclosure can provide a combination of natural cannabinoids grown with the methods described herein. The cannabinoids can be a tetrahydrocannabinol (THC), a cannabidiol (CBD), a cannabinol (CBN), a cannabicyclol (CBL), a cannabichromene (CBC), or another cannabinoid.

The disclosed formulations can comprise one or more pharmaceutically acceptable agents, which alone or in combination solubilize a compound herein or a pharmaceutically acceptable salt thereof.

In some embodiments, a cannabinoid, a pharmaceutically-acceptable salt thereof, a leave, a flower, a steam, or a seed form a plant described herein is present in a formulation in an amount of about 0.1 mg/mL to about 100 mg/mL, about 0.1 mg/mL to about 1 mg/mL, about 0.1 mg/mL to about 5 mg/mL, about 5 mg/mL to about 10 mg/mL, about 10 mg/mL to about 15 mg/mL, about 15 mg/mL to about 20 mg/mL, about 20 mg/mL to about 25 mg/mL, about 25 mg/mL to about 30 mg/mL, about 30 mg/mL to about 35 mg/mL, about 35 mg/mL to about 40 mg/mL, about 40 mg/mL to about 45 mg/mL, about 45 mg/mL to about 50 mg/mL, about 50 mg/mL to about 55 mg/mL, about 55 mg/mL to about 60 mg/mL, about 60 mg/mL to about 65 mg/mL, about 65 mg/mL to about 70 mg/mL, about 70 mg/mL to about 75 mg/mL, about 75 mg/mL to about 80 mg/mL, about 80 mg/mL to about 85 mg/mL, about 85 mg/mL to about 90 mg/mL, about 90 mg/mL to about 95 mg/mL, or about 95 mg/mL to about 100 mg/mL.

In some embodiments, a cannabinoid, a pharmaceutically-acceptable salt thereof, a leave, a flower, a steam, or a seed form a plant described herein is present in a formulation in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL.

A formulation that is disclosed herein can be made more soluble by the addition of an additive or agent. The improvement of solubility of the formulation can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C.

The following table provides non-limiting examples of medicines that are derived from plants. A bioceramic of the disclosure can be used to grown one or more of these plants:

TABLE 2

| Drug/Chemical | Action | Plant Source |
| --- | --- | --- |
| Acetyldigoxin | Cardiotonic | Digitalis lanata (Grecian foxglove, woolly foxglove) |
| Adoniside | Cardiotonic | Adonis vernalis (pheasant's eye, red chamomile) |
| Aescin | Antiinflammatory | Aesculus hippocastanum (horse chestnut) |
| Aesculetin | Antidysentery | Frazinus rhychophylla |
| Agrimophol | Anthelmintic | Agrimonia supatoria |
| Ajmalicine | Treatment for circulatory disorders | Rauvolfia sepentina |
| Allantoin | Vulnerary | Several plants |
| Allyl isothiocyanate | Rubefacient | Brassica nigra (black mustard) |
| Anabesine | Skeletal muscle relaxant | Anabasis sphylla |

TABLE 2-continued

| Drug/Chemical | Action | Plant Source |
|---|---|---|
| Andrographolide | Treatment for baccillary dysentery | Andrographis paniculata |
| Anisodamine | Anticholinergic | Anisodus tanguticus |
| Anisodine | Anticholinergic | Anisodus tanguticus |
| Arecoline | Anthelmintic | Areca catechu (betel nut palm) |
| Asiaticoside | Vulnerary | Centella asiatica (gotu cola) |
| Atropine | Anticholinergic | Atropa belladonna (deadly nightshade) |
| Benzyl benzoate | Scabicide | Several plants |
| Berberine | Treatment for bacillary dysentery | Berberis vulgaris (common barberry) |
| Bergenin | Antitussive | Ardisia japonica (marlberry) |
| Betulinic acid | Anticancerous | Betula alba (common birch) |
| Borneol | Antipyretic, analgesic, antiinflammatory | Several plants |
| Bromelain | Antiinflammatory, proteolytic | Ananas comosus (pineapple) |
| Caffeine | CNS stimulant | Camellia sinensis (tea, also coffee, cocoa and other plants) |
| Camphor | Rubefacient | Cinnamomum camphora (camphor tree) |
| Camptothecin | Anticancerous | Camptotheca acuminata |
| (+)-Catechin | Hemostatic | Potentilla fragarioides |
| Chymopapain | Proteolytic, mucolytic | Carica papaya (papaya) |
| Cissampeline | Skeletal muscle relaxant | Cissampelos pareira (velvet leaf) |
| Cocaine | Local anaesthetic | Erythroxylum coca (coca plant) |
| Codeine | Analgesic, antitussive | Papaver somniferum (poppy) |
| Colchiceine amide | Antitumor agent | Colchicum autumnale (autumn crocus) |
| Colchicine | Antitumor, antigout | Colchicum autumnale (autumn crocus) |
| Convallatoxin | Cardiotonic | Convallaria majalis (lily-of-the-valley) |
| Curcumin | Choleretic | Curcuma longa (turmeric) |
| Cynarin | Choleretic | Cynara scolymus (artichoke) |
| Danthron | Laxative | Cassia species |
| Demecolcine | Antitumor agent | Colchicum autumnale (autumn crocus) |
| Deserpidine | Antihypertensive, tranquilizer | Rauvolfia canescens |
| Deslanoside | Cardiotonic | Digitalis lanata (Grecian foxglove, woolly foxglove) |
| L-Dopa | Anti-parkinsonism | Mucuna species (nescafe, cowage, velvetbean) |
| Digitalin | Cardiotonic | Digitalis purpurea (purple foxglove) |
| Digitoxin | Cardiotonic | Digitalis purpurea (purple foxglove) |
| Digoxin | Cardiotonic | Digitalis purpurea (purple or common foxglove) |
| Emetine | Amoebicide, emetic | Cephaelis ipecacuanha |
| Ephedrine | Sympathomimetic, antihistamine | Ephedra sinica (ephedra, ma huang) |
| Etoposide | Antitumor agent | Podophyllum peltatum (mayapple) |
| Galanthamine | Cholinesterase inhibitor | Lycoris squamigera (magic lily, resurrection lily, naked lady) |
| Gitalin | Cardiotonic | Digitalis purpurea (purple or common foxglove) |
| Glaucarubin | Amoebicide | Simarouba glauca (paradise tree) |
| Glaucine | Antitussive | Glaucium flavum (yellow hornpoppy, horned poppy, sea poppy) |
| Glasiovine | Antidepressant | Octea glaziovii |
| Glycyrrhizin | Sweetener, treatment for Addison's disease | Glycyrrhiza glabra (licorice) |
| Gossypol | Male contraceptive | Gossypiun species (cotton) |
| Hemsleyadin | Treatment for bacillary dysentery | Hemsleya amabilis |
| Hesperidin | Treatment for capillary fragility | Citrus species (e.g., oranges) |
| Hydrastine | Hemostatic, astringent | Hydrastis canadensis (goldenseal) |
| Hyoscyamine | Anticholinergic | Hyoscyamus niger (black henbane, stinking nightshade, henpin) |
| Irinotecan | Anticancer, antitumor agent | Camptotheca acuminata |
| Kaibic acud | Ascaricide | Digenea simplex (wireweed) |
| Kawain | Tranquilizer | Piper methysticum (kava kava) |
| Kheltin | Bronchodilator | Ammi visaga |
| Lanatosides A, B, C | Cardiotonic | Digitalis lanata (Grecian foxglove, woolly foxglove) |
| Lapachol | Anticancer, antitumor | Tabebuia species (trumpet tree) |
| a-Lobeline | Smoking deterrent, respiratory stimulant | Lobelia inflata (Indian tobacco) |
| Menthol | Rubefacient | Mentha species (mint) |
| Methyl salicylate | Rubefacient | Gaultheria procumbens (wintergreen) |
| Monocrotaline | Topical antitumor agent | Crotalaria sessiliflora |
| Morphine | Analgesic | Papaver somniferum (poppy) |
| Neoandrographolide | Treatment of dysentery | Andrographis paniculata |
| Nicotine | Insecticide | Nicotiana tabacum (tobacco) |
| Nordihydroguaiaretic acid | Antioxidant | Larrea divaricata (creosote bush) |
| Noscapine | Antitussive | Papaver somniferum (poppy) |

TABLE 2-continued

| Drug/Chemical | Action | Plant Source |
| --- | --- | --- |
| Ouabain | Cardiotonic | Strophanthus gratus (ouabain tree) |
| Pachycarpine | Oxytocic | Sophora pschycarpa |
| Palmatine | Antipyretic, detoxicant | Coptis japonica (Chinese goldenthread, goldthread, Huang-Lia) |
| Papain | Proteolytic, mucolytic | Carica papaya (papaya) |
| Papavarine | Smooth muscle relaxant | Papaver somniferum (opium poppy, common poppy) |
| Phyllodulcin | Sweetener | Hydrangea macrophylla (bigleaf hydrangea, French hydrangea) |
| Physostigmine | Cholinesterase inhibitor | Physostigma venenosum (Calabar bean) |
| Picrotoxin | Analeptic | Anamirta cocculus (fish berry) |
| Pilocarpine | Parasympathomimetic | Pilocarpus jaborandi (jaborandi, Indian hemp) |
| Pinitol | Expectorant | Several plants (e.g., bougainvillea) |
| Podophyllotoxin | Antitumor, anticancer agent | Podophyllium peltatum (mayapple) |
| Protoveratrines A, B | Antihypertensives | Veratrum album (white false hellebore) |
| Pseudoephredrine | Sympathomimetic | Ephedra sinica (ephedra, ma huang) |
| nor-pseudoephedrine | Sympathomimetic | Ephedra sinica (ephedra, ma huang) |
| Quinidine | Antiarrhythmic | Cinchona ledgeriana (quinine tree) |
| Quinine | Antimalarial, antipyretic | Cinchona ledgeriana (quinine tree) |
| Qulsqualic acid | Anthelmintic | Quisqualis indica (Rangoon creeper, drunken sailor) |
| Rescinnamine | Antihypertensive, tranquilizer | Rauvolfia serpentina |
| Reserpine | Antihypertensive, tranquilizer | Rauvolfia serpentina |
| Rhomitoxin | Antihypertensive, tranquilizer | Rhododendron molle (rhododendron) |
| Rorifone | Antitussive | Rorippa indica |
| Rotenone | Piscicide, Insecticide | Lonchocarpus nicou |
| Rotundine | Analagesic, sedative, traquilizer | Stephania sinica |
| Rutin | Treatment for capillary fragility | Citrus species (e.g., orange, grapefruit) |
| Salicin | Analgesic | Salix alba (white willow) |
| Sanguinarine | Dental plaque inhibitor | Sanguinaria canadensis (bloodroot) |
| Santonin | Ascaricide | Artemisia maritma (wormwood) |
| Scillarin A | Cardiotonic | Urginea maritima (squill) |
| Scopolamine | Sedative | Datura species (e.g., Jimsonweed) |
| Sennosides A, B | Laxative | Cassia species (cinnamon) |
| Silymarin | Antihepatotoxic | Silybum marianum (milk thistle) |
| Sparteine | Oxytocic | Cytisus scoparius (scotch broom) |
| Stevioside | Sweetener | Stevia rebaudiana (stevia) |
| Strychnine | CNS stimulant | Strychnos nux-vomica (poison nut tree) |
| Taxol | Antitumor agent | Taxus brevifolia (Pacific yew) |
| Teniposide | Antitumor agent | Podophyllum peltatum (mayapple or mandrake) |
| Tetrahydrocannabinol (THC) | Antiemetic, decreases occular tension | Cannabis sativa (marijuana) |
| Tetrahydropalmatine | Analgesic, sedative, tranquilizer | Corydalis ambigua |
| Tetrandrine | Antihypertensive | Stephania tetrandra |
| Theobromine | Diuretic, vasodilator | Theobroma cacao (cocoa) |
| Theophylline | Diuretic, bronchodilator | Theobroma cacao and others (cocoa, tea) |
| Thymol | Topical antifungal | Thymus vulgaris (thyme) |
| Topotecan | Antitumor, anticancer agent | Camptotheca acuminata |
| Trichosanthin | Abortifacient | Trichosanthes kirilowii (snake gourd) |
| Tubocuraine | Skeletal muscle relaxant | Chondodendron tomentosum (curare vine) |
| Valapotriates | Sedative | Valeriana officinalis (valerian) |
| Vasicine | Cerebral stimulant | Vinca minor (periwinkle) |
| Vinblastine | Antitumor, Antileukemic agent | Catharanthus roseus (Madagascar periwinkle) |
| Vincristine | Antitumor, Antileukemic agent | Catharanthus roseus (Madagascar periwinkle) |
| Yohimbine | Aphrodisiac | Pausinystalia yohimbe (yohimbe) |
| Yuanhuacine | Abortifacient | Daphne genkwa (lilac) |
| Yuanhuadine | Abortifacient | Daphne genkwa (lilac) |

The following non-limiting examples serves to further illustrate the present invention.

EXAMPLES

Example 1: Preparation of a Bioceramic Powder Composition

A kaolinite is obtained by purchasing it from a mining company/supplier. Optionally, the kaolinite is washed with hydrogen peroxide ($H_2O_2$) and allowed to dry. The dried kaolinite is then finely ground and mixed with tourmaline; aluminum oxide ($Al_2O_3$); silicon dioxide ($SiO_2$); and titanium dioxide ($TiO_2$) until a homogeneous mixture is achieved. The resulting bioceramic composition contains 50 wt % kaolinite, 10 wt % tourmaline, 18 wt % aluminum oxide, 14 wt % silicon dioxide, and 8 wt % titanium dioxide.

Alternatively, the dried kaolinite is finely ground and mixed with tourmaline; aluminum oxide ($Al_2O_3$); silicon dioxide ($SiO_2$); and magnesium oxide (MgO) until a homogeneous mixture is achieved. The resulting bioceramic composition contains 50 wt % kaolinite, 10 wt % tourmaline, 18 wt % aluminum oxide, 14 wt % silicon dioxide, and 8 wt % magnesium oxide.

In yet another embodiment, the dried kaolinite is finely ground and mixed with tourmaline; aluminum oxide ($Al_2O_3$); silicon dioxide ($SiO_2$); and zirconium dioxide ($ZrO_2$) until a homogeneous mixture is achieved. The resulting bioceramic composition contains 50 wt % kaolinite, 10 wt % tourmaline, 18 wt % aluminum oxide, 14 wt % silicon dioxide, and 8 wt % zirconium oxide.

A bioceramic composition was also synthesized. The resulting bioceramic contains any composition described herein, including:
1) about 50% kaolinite, about 10% tourmaline, about 18% aluminum oxide, about 14% silicon dioxide, and about 8% titanium dioxide;
2) about 50% kaolinite, about 10% tourmaline, about 18% aluminum oxide, about 14% silicon dioxide, and about 8% magnesium oxide; or
3) about 50% kaolinite, about 10% tourmaline, about 18% aluminum oxide, about 14% silicon dioxide, and about 8% zirconium dioxide.

Example 2: Growth of a Plant from the Cannabaceae Family in a Substrate with Powdered Bioceramics A bioceramic of the disclosure is a refractory, inorganic, polycrystalline composition that can be reduced to powdered format by grinding, crushing, or another suitable method. In powder form, a bioceramic is added to a substrate used in the growth of the plant.

Select plants are evaluated over a 4 to 6 month growth cycle while exposed to the disclosed bioceramics. Two sample groups will have the bioceramic mixed into the soil at two different stages of the growth cycle of the plant. Two additional groups will receive a placebo treatment (standard treatment) and a group will be exposed to bioceramic treated water. These plants will be evaluated for growth, growth rate, and critical biochemical markers.

Fifty plants will begin the growth cycle at the earliest stage. The 50 well plant starter will be divided into the following quadrants: 12, 12, 13, 13. The table below summarizes how the plants will be processed. TABLE 2 summarizes how the plants will be processed.

For the 10% volume mixture a unit measure of volume is to be used and one unit will be mixed with 9 units of soil. It is expected that the bioceramic, because of its higher density, will settle to the bottom, thus mixing will be conduct to suspend as best can be accomplished.

To create the treated water system, approximately 50 pounds of bioceramic will be placed into the bottom of a 55 gallon plastic drum in which water is deposited. Efforts will be made to insure water circulation to the sediment bed in the bottom of the drum. A circulation system will be used to continually infuse water through the bed for 48 hours before watering. This tank will be isolated and used only for this evaluation. Each treatment will be replenished every 30 days.

Figure 2:
FIG. 2 illustrates two substrate systems.
Figure 2:

FIG. 2 illustrates two substrate systems used in this example. FIG. 2, Panel A illustrates a soil substrate comprising about 1 part volume of a bioceramic to about 9 parts volume of the substrate. FIG. 2, Panel B illustrates a water substrate comprising about 1 part volume of a bioceramic to about 9 parts volume of the substrate.

Figure 3:
FIG. 3 illustrates an overhead picture of a population of *Cannabis indica* clones.

All other conditions; watering frequency, lighting, and others will be normalized to standard procedures. The plants will be of the same strain limiting variations due to plant variations. Microbial and Chemical analysis will be conducted using standard lab procedures. FIG. 3 illustrates an overhead picture of a population of *Cannabis indica* clones.

Example 3: Transplanting a Plant from the Cannabaceae Family in a Substrate with Powdered Bioceramics Purpose: Twelve "Dark Star" *cannabis* plants are being transplanted from one gallon nursery pots (not comprising bioceramics), into seven-gallon nursery pots (comprising bioceramics). The one gallon nursery pots containing the 12 plants have not yet been introduced to the disclosed bioceramics in the soil. Six plants will be chosen at random to receive the bioceramic in the soil, at a rate of 13%, while six different plants will serve as the controls and be planted in plain organic soil.

Figure 4:
FIG. 4 illustrates an overhead picture of young *Cannabis indica* clones transplanted into soil. The three clones illustrated on the right side of the picture are grown in soil comprising the bioceramics described herein (see, e.g., whitish soil color). The three clones illustrated on the left side of the picture are grown in soil without the instant bioceramics.

These plants will be grown in the same room right next to each other. For a period of about 10 to 12 days these plants will be under 18 hours of light, continuing their vegetative state. Thereafter, the plants will be switched to a 12 hours light cycle on, 12 hours light cycle off, initiating their blooming phase. From this moment until harvest the plants will receive a mixture of nutrients and bioceramic infused reverse osmosis water. FIG. 4 illustrates an overhead picture of young *Cannabis indica* clones transplanted into soil as

TABLE 3

Figure 5:
FIG. 5 illustrates a side-by-side comparison of two clones grown under different conditions. The clone on the right was grown on soil comprising the disclosed bioceramics, the clone on the left was grown on soil that did not have the disclosed bioceramics.

| Quadrant | Group A 12 plants | Group B 13 plants | Group C 12 plants | Group D 13 plants |
| --- | --- | --- | --- | --- |
| Phase One Treatment - Plants will be placed in tray, beginning of growth cycle | Baseline - same as current | Treated Water Only | Water | Phase One Treatment - Plants will be placed in tray, beginning of growth cycle |
| Phase Two (larger pot, growth in "Box") & Phase Three (Larger and final Pot in Growth Rooms) | Baseline - same as current | Plant is transferred to pot and treated with the same soil mix as the baseline by with the Water Treatment | Water Treatment & Soil Integration at a 1 to 9 volume/volume mix (10% by volume) | Water Treatment & Soil Integration at a 1 to 4 volume/volume mix (20% by volume) | described above. The three clones illustrated on the right side of the picture are grown in soil comprising the bioceramics described herein (see, e.g., whitish soil color). The three clones illustrated on the left side of the picture are grown in soil without the instant bioceramics. FIG. 5 illustrates a side-by-side comparison of two clones grown under different conditions. The clone on the right was transplanted and grown on soil comprising the disclosed bioceramics. The clone on the left was grown on soil that did not have the disclosed bioceramics.

Method: Organic soil and bioceramics will be mixed using a medium size Rubbermaid container, and mixing will be done by hand for several minutes ensuring a complete and thorough mixture is achieved. Roughly 60 cups of soil will be mixed with eight cups of bioceramic powder. After a couple minutes, the mixture is ready for use and set aside. From 20 "Dark Star" *cannabis* plants, six are chosen at random to be transplanted into bio-ceramic soil. All plants are healthy, green, bug and pathogen free. Four scoops of BC/Soil are put into the bottom of the pot. Plants are pruned up, and then put into the seven-gallon container. The root ball is then surrounded with more BC/Soil, top dressed in Sumatran Bat Guano, then filled with more soil. Plants are then watered (plain Reverse Osmosis water) after transplanting is complete. Plants will be kept in 18 hours of light for roughly 10 days before the light cycle is changed to 12 hours. Plants will be watered as all other plants, with reverse osmosis water and organic fertilizer.

Example 4: *Cannabis* Clones Grown with the Disclosed Bioceramics

Purpose: to transfer clones from mature vegetative *cannabis* plants and introducing bioceramic to these clones. This experiment aims to determine the effect of the disclosed bioceramic in the developmental stage where clones begin to root and become plantings.

Method: 25 clones from 4 different strains (flavors/genetics) of *cannabis*, for a total of 100 clones/immature plants were cut. Clones were placed in 10"×20" white propagation trays holding 50 clones a piece. The peat moss cloning cubes used were re-hydrated in water before being used by soaking the peat moss cubes in a mixture of 5% bioceramic and 95% water. Branches are then selected from a mature plant, cut, dipped in a gel, and placed in the cubes. Cubes sit in a 50-cell tray which fits inside of the 10"×20" propagation tray. A total of two trays were used to house the 100 clones. Two cups of bioceramic were put in the bottom of each tray, and then filled with six cups of Reverse Osmosis water. The propagation trays are kept under fluorescent lights and on top of heat mats, keeping the cubes between 70-80 degrees Fahrenheit. Several clones from the same plants and strains were cut and used as controls (not exposed to a bioceramic).

Example 5: Effect of Bioceramics in the Growth of Organic Produce

Objective: to evaluate the effect of BioPower® on the growth of hydroponic lettuce (*Lactuca sativa Cannabis*).

Methods: experiments were conducted with lettuce (*Lactuca sativa*) cultivated in a hydroponic system. Control group was cultivated following standard hydroponics methodology. Experimental group (bioceramics) was treated with bioceramic pellets (30% bioceramic, 70% polystyrene-polypropylene—1 pound) placed inside the water pump. The lettuce was cultivated for 3 weeks and collected for analyses.

Figure 6:
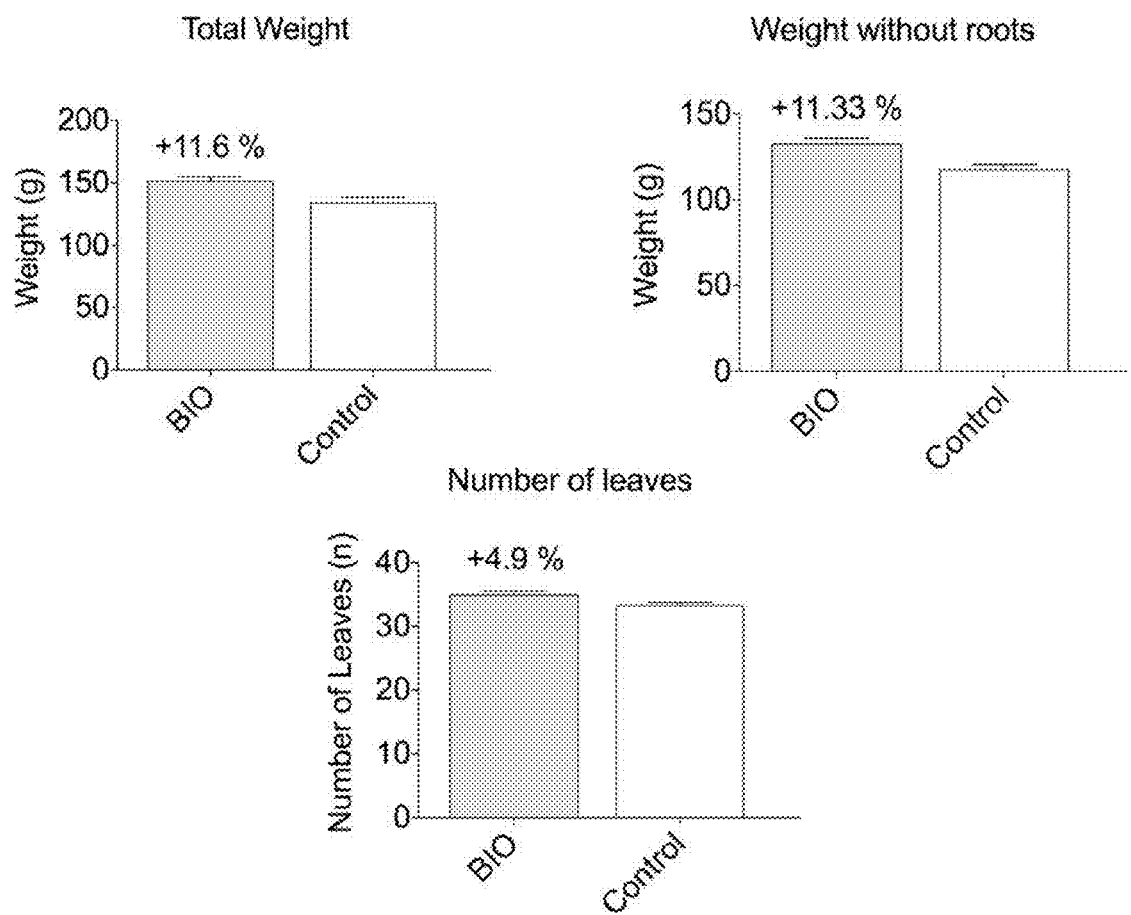
FIG. 6 are non-limiting graphs illustrating the effect of adding bioceramic of the instant disclosure to a water treatment in a hydroponic system.

Results: the results indicate that lettuce that received water treated with bioceramics weighted more and presented more leaves in comparison to control group. FIG. 6 are graphs illustrating the effect of adding bioceramics to a water treatment in a hydroponic system. n=12, the vertical lines indicate the S.E.M.*p<0.05.

Figure 7:
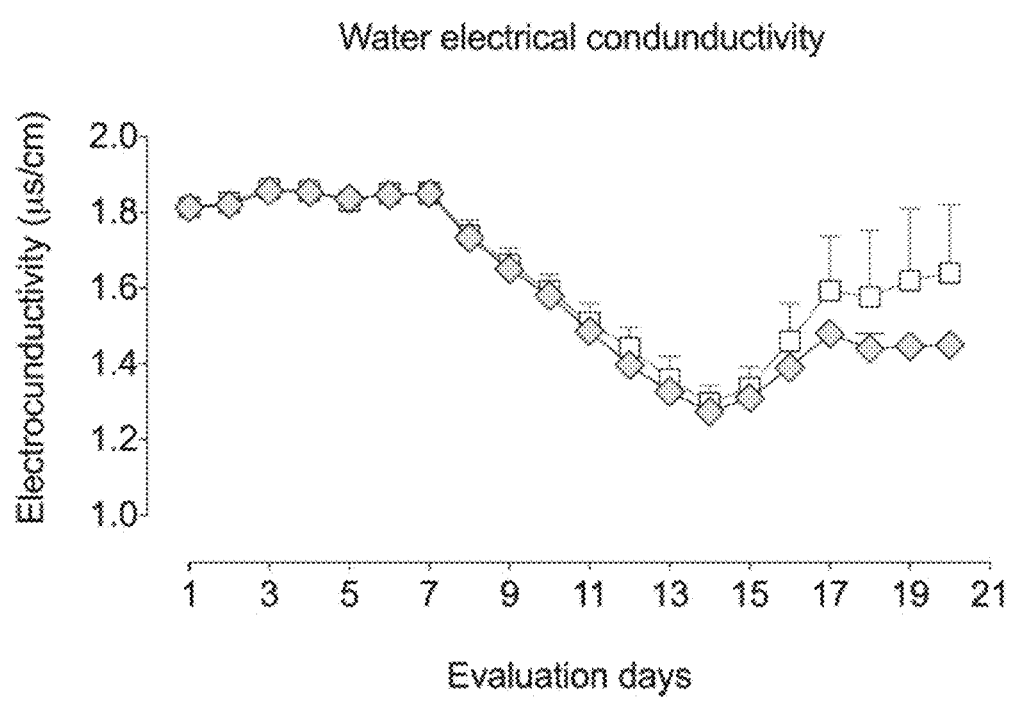
FIG. 7 is a non-limiting example of a graph illustrating the lower electrical conductivity of water treated with bioceramics of the instant disclosure presented from day 16 to 20 in comparison to control group (water only).
Figure 8:
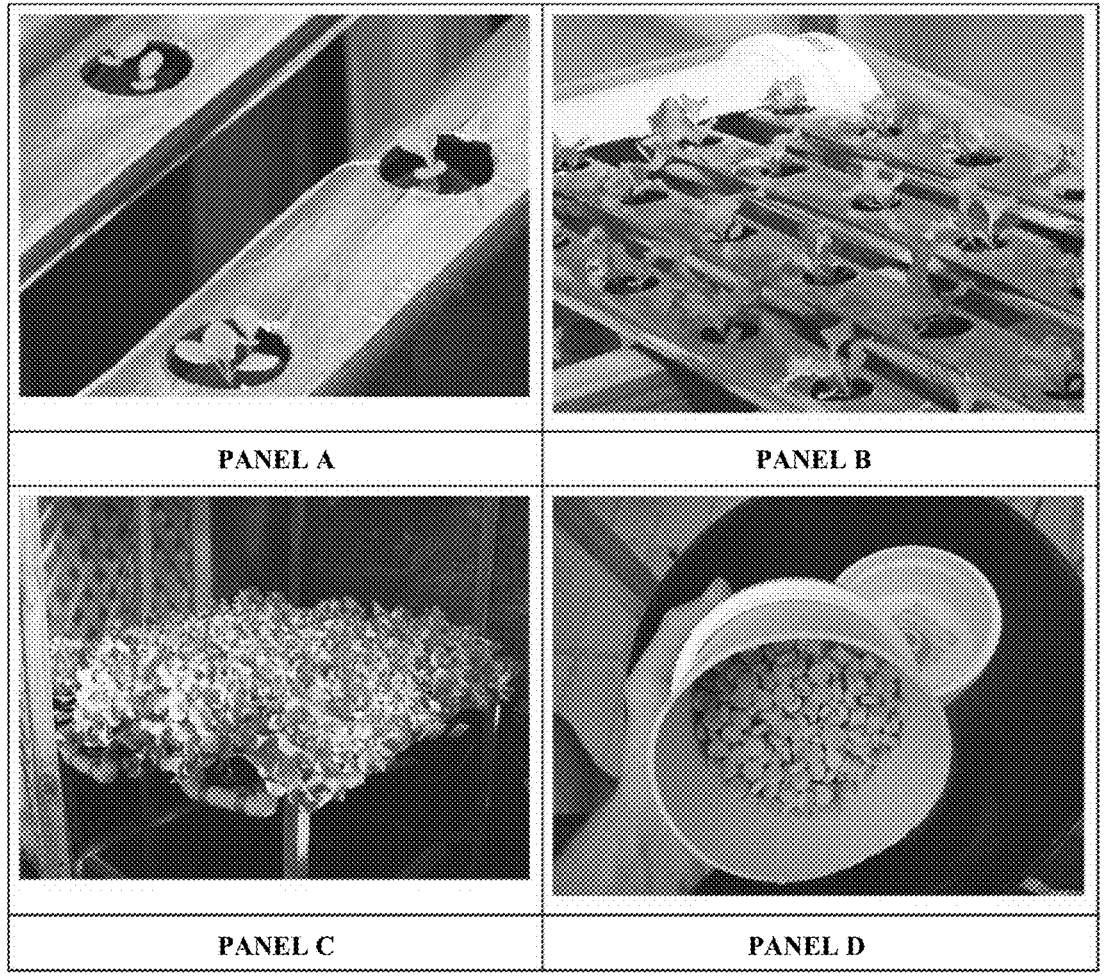
FIG. 8 are non-limiting examples of photographs showing the effect of bioceramics of the instant disclosure in the growth of organic produce.

Electrical conductivity (EC) (displayed in microsiemens (μS)) is a measurement of the nutrient solutions ability to conduct an electrical current. Pure water (deionized water) is an insulator. It is the conductive substances (or ionized salts) dissolved in the water that determine how conductive the solution is. With few exceptions, when there is a greater concentration of nutrients, the electrical current will flow faster, and when there is a lower concentration, the current will flow slower. This is because the quantity of dissolved solids in the nutrient solution is directly proportional to the conductivity. Thus, by measuring the EC, one can determine how strong or weak the concentration of the nutrient solution is. In this case, a lower electrical conductivity in the experimental group (BioPower group) denotes a lower concentration of nutrients in the solution, which may suggest that BioPower treated plants absorbed more nutrients than control group plants. FIG. 7 is a graph illustrating the lower electrical conductivity of water treated with bioceramics presented from day 16 to 20 in comparison to control group (water only). FIG. 8 are photographs showing the lettuce at the start of treatment—1$^{st}$ day in the system (FIG. 8, panel A); the lettuce after the first week of treatment (FIG. 8, panel B); the lettuce after the third week of treatment (FIG. 8, panel C); and a photograph of the bioceramic pellets used in the experiment (FIG. 8, panel D).

Example 6: Infrared Transmittance of Bioceramics

Objective: to compare the infrared transmittance of a bioceramic of the instant disclosure (comprising 18% aluminum oxide, 14% silicon dioxide, 50% kaolinite, 8% zirconium oxide, and 10% tourmaline) to a distinct bioceramic composition (comprising 20% aluminum, 3% titanium, 11% magnesium oxide, 6% diiron trioxide, and 60% silica).

Methods: the infrared transmittance of powdered samples (particle size=about 25 micrometers) of the bioceramic powders was taken using a Bruker spectrometer (Model Spectrum VERTEX 70, OPUS 6.5 software). Transmittance (%) ratings were determined with a resolution of 4 cm$^{-1}$ and 72 scans at a scan range from 350 cm$^{-1}$ to 4000 cm$^{-1}$.

Figure 9:
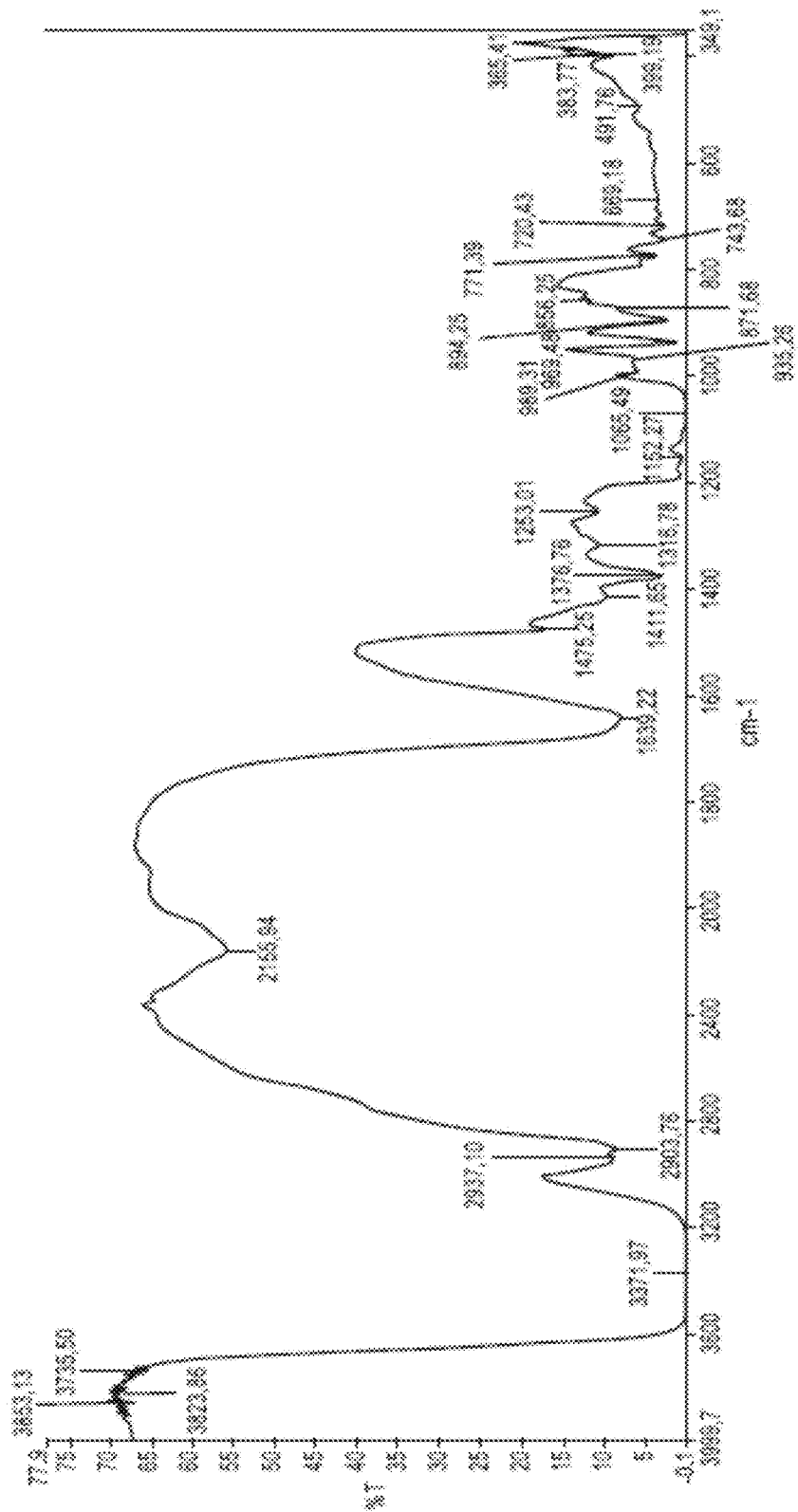
FIG. 9 illustrates the infrared transmittance of a bioceramic composition comprising 18% aluminum oxide, 14% silicon dioxide, 50% kaolinite, 8% zirconium oxide, and 10% tourmaline.
Figure 10:
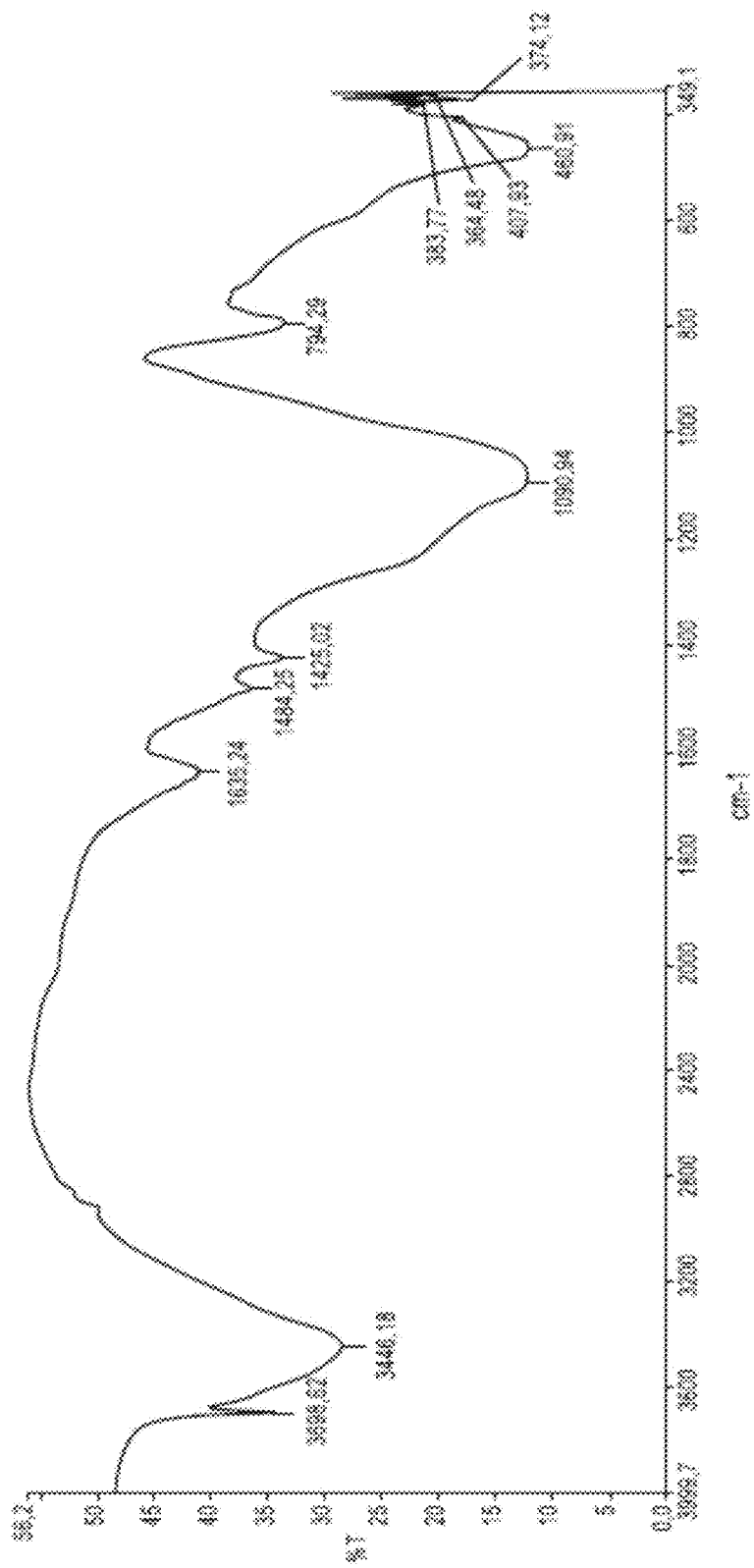
FIG. 10 illustrates the infrared transmittance of a bioceramic composition comprising 20% aluminum, 3% titanium, 11% magnesium oxide, 6% diiron trioxide, and 60% silica.

FIG. 9 illustrates the infrared transmittance of a bioceramic composition comprising 18% aluminum oxide, 14% silicon dioxide, 50% kaolinite, 8% zirconium oxide, and 10% tourmaline. FIG. 10 illustrates the infrared transmittance of a bioceramic composition comprising 20% aluminum, 3% titanium, 11% magnesium oxide, 6% diiron trioxide, and 60% silica.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of growing a plant from the Cannabaceae family on a substrate, the method comprising: cultivating the plant from the Cannabaceae family on the substrate, wherein the substrate comprises:
   a) at most 1 part volume of a kaolinite to about 100 parts volume of the substrate;
   b) at most 1 part volume of a tourmaline to about 100 parts volume of the substrate; and c) at least one of silicon dioxide (SiO$_2$), aluminum oxide (Al$_2$O$_3$), zirconium oxide (ZrO$_2$), titanium dioxide (TiO$_2$), or magnesium oxide (MgO).

2. The method of claim 1, wherein the substrate comprises:
   a) at most 1 part volume of kaolinite to about 50 parts volume of the substrate; and
   b) at most 1 part volume of tourmaline to about 50 parts volume of the substrate.

3. The method of claim 2, wherein the plant from the Cannabaceae family comprises a plant from the *Cannabis* genus.

4. The method of claim 3, wherein the plant from the *Cannabis* genus comprises a *Cannabis sativa* plant.

5. The method of claim 3, wherein the plant from the *Cannabis* genus comprises a *Cannabis indica* plant.

6. The method of claim 3, wherein the plant from the *Cannabis* genus comprises a hybrid plant of two or more *Cannabis* species.

7. The method of claim 1, wherein the substrate comprises less than 10% dry weight of nitrogen (N), phosphorus (P), potassium (K), calcium (Ca), sulfur (S), magnesium (Mg), and sodium (Na).

8. A method of growing a plant from the Cannabaceae family on a substrate, the method comprising: cultivating the plant from the Cannabaceae family on the substrate, wherein the substrate comprises:
   a) at most 1 part volume of a kaolinite to about 100 parts volume of the substrate and at most 1 part volume of a tourmaline to about 100 parts volume of the substrate; and
   b) adding a second quantity of kaolinite and a second quantity of tourmaline to the substrate after a first period of time.

9. The method of claim 8, wherein the first period of time comprises 7 days to 80 days, 20 days to 60 days, 20 days to 40 days, or combinations thereof.

10. The method of claim 8, wherein the substrate comprises:
    a) at most 1 part volume of kaolinite to about 50 parts volume of the substrate; and
    b) at most 1 part volume of tourmaline to about 50 parts volume of the substrate.

11. The method of claim 8, wherein the plant from the Cannabaceae family comprises a plant from the *Cannabis* genus.

12. The method of claim 11, wherein the plant from the *Cannabis* genus comprises a *Cannabis sativa* plant.

13. The method of claim 11, wherein the plant from the *Cannabis* genus comprises a *Cannabis indica* plant.

14. The method of claim 11, wherein the plant from the *Cannabis* genus comprises a hybrid plant of two or more *Cannabis* species.

15. The method of claim 8, wherein the substrate comprises less than 10% dry weight of nitrogen (N), phosphorus (P), potassium (K), calcium (Ca), sulfur (S), magnesium (Mg), and sodium (Na).

* * * * *